US008048657B2

(12) United States Patent
Breneman et al.

(10) Patent No.: US 8,048,657 B2
(45) Date of Patent: Nov. 1, 2011

(54) ENZYME COMPOSITIONS COMPRISING A GLUCOAMYLASE, AN ACID STABLE ALPHA AMYLASE, AND AN ACID FUNGAL PROTEASE

(75) Inventors: Suzanne Breneman, Orfordville, WI (US); Oreste J. Lantero, Jr., Trimble, MO (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 321 days.

(21) Appl. No.: 12/250,789

(22) Filed: Oct. 14, 2008

(65) Prior Publication Data

US 2009/0203101 A1 Aug. 13, 2009

Related U.S. Application Data

(60) Provisional application No. 60/981,035, filed on Oct. 18, 2007.

(51) Int. Cl.
| | |
|---|---|
| *C12P 7/14* | (2006.01) |
| *C12N 9/00* | (2006.01) |
| *C12N 9/30* | (2006.01) |
| *C12N 9/34* | (2006.01) |
| *C12N 1/20* | (2006.01) |
| *C12N 15/00* | (2006.01) |

(52) U.S. Cl. ........ 435/162; 435/183; 435/203; 435/205; 435/252.3; 435/320.1; 536/23.2

(58) Field of Classification Search ........................ None
See application file for complete search history.

(56) References Cited

U.S. PATENT DOCUMENTS

| | | | |
|---|---|---|---|
| 4,092,434 | A | 5/1978 | Yoshizuma et al. |
| 4,514,496 | A | 4/1985 | Yoshizumi et al. |
| RE32,153 | E | 5/1986 | Tamura et al. |
| 4,587,215 | A | 5/1986 | Hirsh |
| 4,618,579 | A | 10/1986 | Dwiggins |
| 4,760,025 | A | 7/1988 | Estell et al. |
| 5,000,000 | A | 3/1991 | Ingram et al. |
| 5,028,539 | A | 7/1991 | Ingram et al. |
| 5,424,202 | A | 6/1995 | Ingram et al. |
| 5,514,583 | A | 5/1996 | Picataggio et al. |
| 5,554,520 | A | 9/1996 | Fowler et al. |
| 5,612,055 | A | 3/1997 | Bedford et al. |
| 6,352,851 | B1 | 3/2002 | Nielsen et al. |
| 7,205,138 | B2 | 4/2007 | Dunn-Coleman et al. |
| 2006/0003408 | A1 * | 1/2006 | Dunn-Coleman et al. ... 435/69.1 |
| 2006/0094080 | A1 | 5/2006 | Dunn-Coleman et al. |

FOREIGN PATENT DOCUMENTS

| | | |
|---|---|---|
| WO | WO 92/00381 | 1/1992 |
| WO | WO 92/06209 | 4/1992 |
| WO | WO 95/13362 | 5/1995 |
| WO | WO 97/20950 | 6/1997 |
| WO | WO 99/28488 | 6/1999 |
| WO | WO 00/04136 | 1/2000 |
| WO | WO 02/074895 A2 | 9/2002 |
| WO | WO 2004/080923 A2 | 9/2004 |
| WO | WO 2005/052148 | 6/2005 |
| WO | WO 2006/003408 A1 | 1/2006 |
| WO | WO 2006/060062 * | 6/2006 |
| WO | WO 2006/060062 A2 | 6/2006 |
| WO | WO 2006/073839 A2 | 7/2006 |
| WO | WO 2006/089107 A1 | 8/2006 |

OTHER PUBLICATIONS

Accession Q2WBH2, published Jan. 10, 2006.*
Altschul, S.F. et al. "Local alignment statistics." *Methods Enzymol* 266: 460-480, 1993.
Altschul, Stephen F. et al., "Basic Local Alignment Search Tool," J. Mol. Biol. 215:403-410, 1990.
Altschul, Stephen F. et al., "Gapped BLAST and PSI-BLAST: a new generation of protein database search programs," Nucl. Acids Res., vol. 25, pp. 3389-3402, 1997.
Boel et al., "Glucoamylases G1 and G2 from *Aspergillus niger* are synthesized from two different but closely related mRNAs," *The EMBO J.*, V. 3, N. 5, pp. 1097-1102, 1984.
Chen, H.M. et al. "Substitution of asparagine residues in *Aspergillus awamori* glucoamylase by site-directed mutagenesis to eliminate N-glycosylation and inactivation by deamidation," *Biochem. J.*, 301, (Pt 1):275-281 (1994).
Chen, H.M. et al. "Identification and elimination by site-directed mutagenesis of thermolabile aspartyl bonds in *Aspergillus awamori* glucoamylase," *Protein Eng.*, 8(6):575-582, (1995).
Chen, H.-M. et al. "Effect of replacing helical glycine residues with alanines on reversible and irreversible stability and production of *Aspergillus awamori* glucoamylase," *Protein Eng.*, 9(6):499-505 (1996).
Dayhoff, M.O. et al., "A Model of Evolutionary Change in Proteins," Atlas of Protein Sequence and Structure, National Biomedical Research Foundation, Washington, D.C., vol. 5, Supplement 3, Chapter 22, pp. 345-352 1978.
Hata, Y. et al. "The glucoamylase cDNA from *Aspergillus oryzae*: Its cloning, nucleotide sequence, and expression in *Saccharomyces cerevisiae*," *Agric. Biol. Chem.*, 55(4):941-949 (1991).
Jensen, B. et al. "Purification of extracellular amylolytic enzymes from the thermophilic fungus *Thermomyces lanuginosus*," *Can. J. Microbiol.*, 34(3):218-223 (1988).
Miller, G.L. "Use of Dinitrosalicylic Acid Reagent for Determination of Reducing Sugar," *Anal. Chem.*, 31(3):426-428 (1959).
Needleman, S.B. et al. "A general method applicable to the search for similarities in the amino acid sequence of two proteins." *J. Mol. Biol* 48(3): 443-453, Mar. 1970.

(Continued)

*Primary Examiner* — Christian Fronda

(57) ABSTRACT

The present invention relates to an enzyme blend composition comprising a glucoamylase, an acid stable alpha amylase, and an acid fungal protease. The present invention is further directed to a method for producing end products such as alcohols from fermentable sugars, comprising the steps of: (a) contacting a slurry comprising a milled grain that contains starch with an alpha amylase to produce a liquefact; (b) contacting the liquefact with a glucoamylase, an acid stable alpha amylase, and an acid fungal protease, to produce fermentable sugars; and (c) fermenting the fermentable sugars in the presence of a fermenting organism to produce end products.

18 Claims, 1 Drawing Sheet

OTHER PUBLICATIONS

Pearson, W.R. et al. "Improved Tools for Biological Sequence Comparison." *Proc. Natl. Acad. Sci. USA* 85(8): 2444-2448, Apr. 15, 1988.

Smith should be "Shpaer", "GeneAssist—Smith Waterman and Other Database Similarity Searches and Identification of Motifs," *Methods in Molecular Biology, Sequence Data Anaylsis Guidebook*, Humana Press, Inc. 70:173-187 (1997).

Smith, T.F. et al. "Comparison of biosequences." *Adv. Appl. Math* 2: 482-489, 1981.

Taylor et al., "Some properties of a glucoamylase produced by the thermophilic fungus humicola lanuginose," *Carbohydrate Research*, 61 (1978) 301-308.

* cited by examiner

SEQUENCE LISTING

<160> NUMBER OF SEQ ID NOS: 14

<210> SEQ ID NO 1
<211> LENGTH: 599
<212> TYPE: PRT
<213> ORGANISM: Trichoderma reesei

<400> SEQUENCE: 1

```
Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365
```

```
Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
            500                 505                 510

Val Lys Val Ala Gly Asn Ala Ala Ala Leu Gly Asn Trp Ser Thr Ser
        515                 520                 525

Ala Ala Val Ala Leu Asp Ala Val Asn Tyr Ala Asp Asn His Pro Leu
    530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 2
<211> LENGTH: 453
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140
```

```
Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
                260                 265                 270

Pro Cys Ser Asp Lys Ala Leu Ser Asn Leu Lys Val Val Asp Ser
            275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
                420                 425                 430

Arg Ala Gly Ile Val Pro Pro Ser Trp Ala Asn Ser Ser Ala Ser Thr
            435                 440                 445

Ile Pro Ser Thr Cys
450

<210> SEQ ID NO 3
<211> LENGTH: 38
<212> TYPE: PRT
<213> ORGANISM: Trichoderma reesei

<400> SEQUENCE: 3

Ser Gly Ala Ser Val Val Gly Ser Tyr Ser Arg Pro Thr Ala Thr Ser
1               5                   10                  15

Phe Pro Pro Ser Gln Thr Pro Lys Pro Gly Val Pro Ser Gly Thr Pro
            20                  25                  30

Tyr Thr Pro Leu Pro Cys
        35

<210> SEQ ID NO 4
```

```
<211> LENGTH: 108
<212> TYPE: PRT
<213> ORGANISM: Trichoderma reesei

<400> SEQUENCE: 4

Ala Thr Pro Thr Ser Val Ala Val Thr Phe His Glu Leu Val Ser Thr
 1               5                  10                  15

Gln Phe Gly Gln Thr Val Lys Val Ala Gly Asn Ala Ala Ala Leu Gly
            20                  25                  30

Asn Trp Ser Thr Ser Ala Ala Val Ala Leu Asp Ala Val Asn Tyr Ala
        35                  40                  45

Asp Asn His Pro Leu Trp Ile Gly Thr Val Asn Leu Glu Ala Gly Asp
    50                  55                  60

Val Val Glu Tyr Lys Tyr Ile Asn Val Gly Gln Asp Gly Ser Val Thr
65                  70                  75                  80

Trp Glu Ser Asp Pro Asn His Thr Tyr Thr Val Pro Ala Val Ala Cys
                85                  90                  95

Val Thr Gln Val Val Lys Glu Asp Thr Trp Gln Ser
            100                 105

<210> SEQ ID NO 5
<211> LENGTH: 619
<212> TYPE: PRT
<213> ORGANISM: Aspergillus kawachii

<400> SEQUENCE: 5

Leu Ser Ala Ala Glu Trp Arg Thr Gln Ser Ile Tyr Phe Leu Leu Thr
 1               5                  10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Glu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240
```

```
Pro Tyr Gln Lys Tyr Leu Asp Gly Val Leu Asn Tyr Pro Ile Tyr Trp
            245                 250                 255

Gln Leu Leu Tyr Ala Phe Glu Ser Ser Gly Ser Ile Ser Asn Leu
        260                 265                 270

Tyr Asn Met Ile Lys Ser Val Ala Ser Asp Cys Ser Asp Pro Thr Leu
    275                 280                 285

Leu Gly Asn Phe Ile Glu Asn His Asp Asn Pro Arg Phe Ala Ser Tyr
290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Asp Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Asp Tyr Ile Thr Tyr Ala Asn
    370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Asn
        435                 440                 445

Gly Asp Ile Pro Val Pro Met Ala Ser Gly Leu Pro Arg Val Leu Leu
    450                 455                 460

Pro Ala Ser Val Val Asp Ser Ser Leu Cys Gly Gly Ser Gly Asn
465                 470                 475                 480

Thr Thr Thr Thr Thr Thr Ala Ala Thr Ser Thr Ser Lys Ala Thr Thr
                485                 490                 495

Ser Ser Ser Ser Ser Ala Ala Thr Thr Ser Ser Ser Cys Thr
            500                 505                 510

Ala Thr Ser Thr Thr Leu Pro Ile Thr Phe Glu Glu Leu Val Thr Thr
        515                 520                 525

Thr Tyr Gly Glu Glu Val Tyr Leu Ser Gly Ser Ile Ser Gln Leu Gly
    530                 535                 540

Glu Trp Asp Thr Ser Asp Ala Val Lys Leu Ser Ala Asp Asp Tyr Thr
545                 550                 555                 560

Ser Ser Asn Pro Glu Trp Ser Val Thr Val Ser Leu Pro Val Gly Thr
                565                 570                 575

Thr Phe Glu Tyr Lys Phe Ile Lys Val Asp Glu Gly Gly Ser Val Thr
            580                 585                 590

Trp Glu Ser Asp Pro Asn Arg Glu Tyr Thr Val Pro Glu Cys Gly Ser
        595                 600                 605

Gly Ser Gly Glu Thr Val Val Asp Thr Trp Arg
    610                 615

<210> SEQ ID NO 6
<211> LENGTH: 37
<212> TYPE: PRT
<213> ORGANISM: Aspergillus kawachii

<400> SEQUENCE: 6
```

```
Thr Thr Thr Thr Thr Thr Ala Ala Thr Ser Thr Ser Lys Ala Thr Thr
1               5                   10                  15

Ser Ser Ser Ser Ser Ser Ala Ala Thr Thr Ser Ser Ser Cys Thr
            20                  25                  30

Ala Thr Ser Thr Thr
            35

<210> SEQ ID NO 7
<211> LENGTH: 480
<212> TYPE: PRT
<213> ORGANISM: Aspergillus kawachii

<400> SEQUENCE: 7

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Glu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Lys Tyr Leu Asp Gly Val Leu Asn Tyr Pro Ile Tyr Trp
                245                 250                 255

Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335
```

```
Gly Gly Asp Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Asp Tyr Ile Thr Tyr Ala Asn
    370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Asn
        435                 440                 445

Gly Asp Ile Pro Val Pro Met Ala Ser Gly Leu Pro Arg Val Leu Leu
    450                 455                 460

Pro Ala Ser Val Val Asp Ser Ser Leu Cys Gly Gly Ser Gly Asn
465                 470                 475                 480
```

<210> SEQ ID NO 8
<211> LENGTH: 102
<212> TYPE: PRT
<213> ORGANISM: Aspergillus kawachii

<400> SEQUENCE: 8

```
Leu Pro Ile Thr Phe Glu Glu Leu Val Thr Thr Tyr Gly Glu Glu
1               5                   10                  15

Val Tyr Leu Ser Gly Ser Ile Ser Gln Leu Gly Glu Trp Asp Thr Ser
            20                  25                  30

Asp Ala Val Lys Leu Ser Ala Asp Asp Tyr Thr Ser Ser Asn Pro Glu
        35                  40                  45

Trp Ser Val Thr Val Ser Leu Pro Val Gly Thr Thr Phe Glu Tyr Lys
    50                  55                  60

Phe Ile Lys Val Asp Glu Gly Gly Ser Val Thr Trp Glu Ser Asp Pro
65                  70                  75                  80

Asn Arg Glu Tyr Thr Val Pro Glu Cys Gly Ser Gly Ser Gly Glu Thr
                85                  90                  95

Val Val Asp Thr Trp Arg
            100
```

<210> SEQ ID NO 9
<211> LENGTH: 616
<212> TYPE: PRT
<213> ORGANISM: Aspergillus niger

<400> SEQUENCE: 9

```
Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
```

```
                    85                  90                  95
Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
        130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Glu Tyr Leu Asp Gly Val Leu Asn Tyr Pro Ile Tyr Trp
                245                 250                 255

Gln Leu Leu Tyr Ala Phe Glu Ser Ser Ser Gly Ser Ile Ser Asp Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Ala Tyr Ile Thr Tyr Ala Asn
    370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
        435                 440                 445

Gly Asp Ile Pro Val Pro Met Ala Ser Gly Leu Pro Arg Val Leu Leu
    450                 455                 460

Pro Ala Ser Val Val Asp Ser Ser Ser Leu Cys Gly Gly Ser Gly Ser
465                 470                 475                 480

Asn Ser Ser Thr Thr Thr Thr Thr Ala Thr Ser Ser Ser Thr Ala
                485                 490                 495

Thr Ser Lys Ser Ala Ser Thr Ser Ser Thr Ser Thr Ala Cys Thr Ala
            500                 505                 510
```

```
Thr Ser Thr Ser Leu Ala Val Thr Phe Glu Glu Leu Val Thr Thr Thr
        515                 520                 525

Tyr Gly Glu Glu Ile Tyr Leu Ser Gly Ser Ile Ser Gln Leu Gly Asp
        530                 535                 540

Trp Asp Thr Ser Asp Ala Val Lys Met Ser Ala Asp Asp Tyr Thr Ser
545                 550                 555                 560

Ser Asn Pro Glu Trp Ser Val Thr Val Thr Leu Pro Val Gly Thr Thr
                565                 570                 575

Phe Glu Tyr Lys Phe Ile Lys Val Glu Ser Asp Gly Thr Val Thr Trp
                580                 585                 590

Glu Ser Asp Pro Asn Arg Glu Tyr Thr Val Pro Glu Cys Gly Ser Gly
                595                 600                 605

Glu Thr Val Val Asp Thr Trp Arg
        610                 615

<210> SEQ ID NO 10
<211> LENGTH: 478
<212> TYPE: PRT
<213> ORGANISM: Aspergillus niger

<400> SEQUENCE: 10

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Glu Tyr Leu Asp Gly Val Leu Asn Tyr Pro Ile Tyr Trp
                245                 250                 255

Gln Leu Leu Tyr Ala Phe Glu Ser Ser Ser Gly Ser Ile Ser Asp Leu
            260                 265                 270
```

```
Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
        290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Gln His Tyr Ser
                325                 330                 335

Gly Gly Lys Val Pro Tyr Asn Arg Glu Ala Thr Trp Leu Ser Gly Tyr
                340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Ala Tyr Ile Thr Tyr Ala Asn
        370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
                420                 425                 430

Lys Leu Ile Glu Ala Tyr Thr Cys Thr Ser Val Thr Val Asp Ser Ser
                435                 440                 445

Gly Asp Ile Pro Val Pro Met Ala Ser Gly Leu Pro Arg Val Leu Leu
                450                 455                 460

Pro Ala Ser Val Val Asp Ser Ser Leu Cys Gly Gly Ser
465                 470                 475

<210> SEQ ID NO 11
<211> LENGTH: 31
<212> TYPE: PRT
<213> ORGANISM: Aspergillus niger

<400> SEQUENCE: 11

Gly Ser Asn Ser Ser Thr Thr Thr Thr Thr Ala Thr Ser Ser Ser
1               5                   10                  15

Thr Ala Thr Ser Lys Ser Ala Ser Thr Ser Ser Thr Ser Thr Ala
                20                  25                  30

<210> SEQ ID NO 12
<211> LENGTH: 107
<212> TYPE: PRT
<213> ORGANISM: Aspergillus niger

<400> SEQUENCE: 12

Cys Thr Ala Thr Ser Thr Ser Leu Ala Val Thr Phe Glu Glu Leu Val
1               5                   10                  15

Thr Thr Thr Tyr Gly Glu Glu Ile Tyr Leu Ser Gly Ser Ile Ser Gln
                20                  25                  30

Leu Gly Asp Trp Asp Thr Ser Asp Ala Val Lys Met Ser Ala Asp Asp
                35                  40                  45

Tyr Thr Ser Ser Asn Pro Glu Trp Ser Val Thr Val Thr Leu Pro Val
50                  55                  60

Gly Thr Thr Phe Glu Tyr Lys Phe Ile Lys Val Glu Ser Asp Gly Thr
65                  70                  75                  80

Val Thr Trp Glu Ser Asp Pro Asn Arg Glu Tyr Thr Val Pro Glu Cys
                85                  90                  95

Gly Ser Gly Glu Thr Val Val Asp Thr Trp Arg
```

<210> SEQ ID NO 13
<211> LENGTH: 443
<212> TYPE: PRT
<213> ORGANISM: Trichoderma reesei

<400> SEQUENCE: 13

```
Asp Thr Ala Ala Trp Arg Ser Arg Thr Ile Tyr Phe Ala Leu Thr Asp
  1               5                  10                  15

Arg Ile Ala Arg Gly Ser Gly Asp Thr Gly Gly Ser Ala Cys Gly Asn
             20                  25                  30

Leu Gly Asp Tyr Cys Gly Gly Thr Phe Gln Gly Leu Glu Ser Lys Leu
         35                  40                  45

Asp Tyr Ile Lys Gly Met Gly Phe Asp Ala Ile Trp Ile Thr Pro Val
     50                  55                  60

Val Thr Ser Asp Asp Gly Gly Tyr His Gly Tyr Trp Ala Glu Asp Ile
 65                  70                  75                  80

Asp Ser Ile Asn Ser His Tyr Gly Ser Ala Asp Asp Leu Lys Ser Leu
                 85                  90                  95

Val Asn Ala Ala His Ser Lys Gly Phe Tyr Met Met Val Asp Val Val
            100                 105                 110

Ala Asn His Met Gly Tyr Ala Asn Ile Ser Asp Asp Ser Pro Ser Pro
        115                 120                 125

Leu Asn Gln Ala Ser Ser Tyr His Pro Glu Cys Asp Ile Asp Tyr Asn
    130                 135                 140

Asn Gln Thr Ser Val Glu Asn Cys Trp Ile Ser Gly Leu Pro Asp Leu
145                 150                 155                 160

Asn Thr Gln Ser Ser Thr Ile Arg Ser Leu Tyr Gln Asp Trp Val Ser
                165                 170                 175

Asn Leu Val Ser Thr Tyr Gly Phe Asp Gly Val Arg Ile Asp Thr Val
            180                 185                 190

Lys His Val Glu Gln Asp Tyr Trp Pro Gly Phe Val Asn Ala Thr Gly
        195                 200                 205

Val Tyr Cys Ile Gly Glu Val Phe Asp Gly Asp Pro Asn Tyr Leu Leu
    210                 215                 220

Pro Tyr Ala Ser Leu Met Pro Gly Leu Leu Asn Tyr Ala Ile Tyr Tyr
225                 230                 235                 240

Pro Met Thr Arg Phe Phe Leu Gln Gln Gly Ser Ser Gln Asp Met Val
                245                 250                 255

Asn Met His Asp Gln Ile Gly Ser Met Phe Pro Asp Pro Thr Ala Leu
            260                 265                 270

Gly Thr Phe Val Asp Asn His Asp Asn Pro Arg Phe Leu Ser Ile Lys
        275                 280                 285

Asn Asp Thr Ala Leu Leu Lys Asn Ala Leu Thr Tyr Thr Ile Leu Ser
    290                 295                 300

Arg Gly Ile Pro Ile Val Tyr Tyr Gly Thr Glu Gln Ala Phe Ser Gly
305                 310                 315                 320

Gly Asn Asp Pro Ala Asn Arg Glu Asp Leu Trp Arg Ser Gly Phe Asn
                325                 330                 335

Ala Gln Ser Asp Met Tyr Asp Ala Ile Ser Lys Leu Tyr Ala Lys
            340                 345                 350

His Ala Val Gly Gly Leu Ala Asp Asn Asp His Lys His Leu Tyr Val
        355                 360                 365

Ala Asp Thr Ala Tyr Ala Phe Ser Arg Ala Gly Gly Asn Met Val Ala
```

```
                    370             375             380
Leu Thr Thr Asn Ser Gly Ser Gly Ser Ser Ala Gln His Cys Phe Gly
385                 390             395                 400

Thr Gln Val Pro Asn Gly Arg Trp Gln Asn Val Phe Asp Glu Gly Asn
                405             410                 415

Gly Pro Thr Tyr Ser Ala Asp Gly Asn Gly Gln Leu Cys Leu Asn Val
                420             425                 430

Ser Asn Gly Gln Pro Ile Val Leu Leu Ser Ser
                435             440

<210> SEQ ID NO 14
<211> LENGTH: 355
<212> TYPE: PRT
<213> ORGANISM: Trichoderma reesei

<400> SEQUENCE: 14

Lys Tyr Gly Ala Pro Ile Ser Asp Asn Leu Lys Ser Leu Val Ala Ala
1               5                   10                  15

Arg Gln Ala Lys Gln Ala Leu Ala Lys Arg Gln Thr Gly Ser Ala Pro
                20                  25                  30

Asn His Pro Ser Asp Ser Ala Asp Ser Glu Tyr Ile Thr Ser Val Ser
            35                  40                  45

Ile Gly Thr Pro Ala Gln Val Leu Pro Leu Asp Phe Asp Thr Gly Ser
        50                  55                  60

Ser Asp Leu Trp Val Phe Ser Ser Glu Thr Pro Lys Ser Ser Ala Thr
65                  70                  75                  80

Gly His Ala Ile Tyr Thr Pro Ser Lys Ser Thr Ser Lys Lys Val
                85                  90                  95

Ser Gly Ala Ser Trp Ser Ile Ser Tyr Gly Asp Gly Ser Ser Ser
                100                 105                 110

Gly Asp Val Tyr Thr Asp Lys Val Thr Ile Gly Gly Phe Ser Val Asn
                115                 120                 125

Thr Gln Gly Val Glu Ser Ala Thr Arg Val Ser Thr Glu Phe Val Gln
            130                 135                 140

Asp Thr Val Ile Ser Gly Leu Val Gly Leu Ala Phe Asp Ser Gly Asn
145                 150                 155                 160

Gln Val Arg Pro His Pro Gln Lys Thr Trp Phe Ser Asn Ala Ala Ser
                165                 170                 175

Ser Leu Ala Glu Pro Leu Phe Thr Ala Asp Leu Arg His Gly Gln Asn
                180                 185                 190

Gly Ser Tyr Asn Phe Gly Tyr Ile Asp Thr Ser Val Ala Lys Gly Pro
            195                 200                 205

Val Ala Tyr Thr Pro Val Asp Asn Ser Gln Gly Phe Trp Glu Phe Thr
        210                 215                 220

Ala Ser Gly Tyr Ser Val Gly Gly Lys Leu Asn Arg Asn Ser Ile
225                 230                 235                 240

Asp Gly Ile Ala Asp Thr Gly Thr Thr Leu Leu Leu Leu Asp Asp Asn
                245                 250                 255

Val Val Asp Ala Tyr Tyr Ala Asn Val Gln Ser Ala Gln Tyr Asp Asn
                260                 265                 270

Gln Gln Glu Gly Val Val Phe Asp Cys Asp Glu Asp Leu Pro Ser Phe
            275                 280                 285

Ser Phe Gly Val Gly Ser Ser Thr Ile Thr Ile Pro Gly Asp Leu Leu
        290                 295                 300

Asn Leu Thr Pro Leu Glu Glu Gly Ser Ser Thr Cys Phe Gly Gly Leu
```

```
                 305                 310                 315                 320

Gln Ser Ser Ser Gly Ile Gly Ile Asn Ile Phe Gly Asp Val Ala Leu
                325                 330                 335

Lys Ala Ala Leu Val Val Phe Asp Leu Gly Asn Glu Arg Leu Gly Trp
            340                 345                 350

Ala Gln Lys
        355
```

ENZYME COMPOSITIONS COMPRISING A GLUCOAMYLASE, AN ACID STABLE ALPHA AMYLASE, AND AN ACID FUNGAL PROTEASE

This application claims the benefit of U.S. Provisional Application No. 60/981,035, filed Oct. 18, 2007; which is incorporated herein by reference in its entirety.

FIELD OF THE INVENTION

The present invention relates to an enzyme blend comprising a glucoamylase, an acid stable alpha amylase, and an acid fungal protease. The present invention also relates to methods of utilizing the enzyme blend in starch conversion processes e.g., such as for producing end products such as ethanol.

BACKGROUND OF THE INVENTION

Industrial fermentation predominantly uses glucose as a feedstock for the production of a multitude of end products such as enzymes, proteins, amino acids, organic acids, sugar alcohols, pharmaceuticals and other biochemicals. In many applications glucose is produced from the enzymatic conversion of substrates comprising starch and cellulose (e.g. whole milled cereal grains). Starch, which comprises two polysaccharide fractions, amylose and amylopectin, is deposited in plant cells as granular particles. The partial crystalline structure of these granules imparts insolubility in cold water, and, as a result, solubilization of starch granules in water generally requires heat energy to disrupt the crystalline structure of the granule. Numerous processes have been employed for starch solubilization and these include direct and indirect heating of substrates comprising granular starch. (See, for example, STARCH CHEMISTRY AND TECHNOLOGY, Eds R. L. Whistler et al., $2^{nd}$ Ed., 1984 Academic Press Inc., Orlando Fla. and STARCH CONVERSION TECHNOLOGY, Eds G. M. A. Van Beynum et al., Food Science and Technology Series 1985 Marcel Dekker Inc. NY).

Starch to glucose processing generally consists of two steps and these steps include liquefaction of starch and saccharification of the liquefied starch. Further steps can include (a) purification and isomerization when the desired end product is a purified dextrose or fructose or (b) fermentation and distillation when the desired end product is, for example an alcohol (e.g., ethanol).

An object of the starch liquefaction process is to convert a slurry of starch polymer granules into a solution of shorter chain length dextrins of low viscosity. This is an important step for convenient handling of industrial equipment used in starch conversion processes. Commonly, the starch is liquefied by use of high temperature and enzymatic bioconversion. For example, a common enzymatic liquefaction process involves adding a thermostable bacterial alpha amylase (e.g. SPEZYME® PRIME and SPEZYME® FRED, SPEZYME® ETHYL (Danisco U.S., Inc, Genencor Division) or TERMAMYL SC, TERMAMYL SUPRA or TERMANYL 120L (Novozymes)) to a slurry comprising a substrate including starch and adjusting the pH to between 5.5 to 6.5 and the temperature to greater than 90° C. The starch is liquified and then subjected to saccharifying enzymes. Typically, saccharification takes place in the presence of glucoamylase enzymes such as glucoamylase from *Aspergillus niger* (e.g., OPTIDEX L-400 (Genencor International Inc.)) at a pH more acidic than the pH of the liquefaction step.

A number of variations exist for the liquefaction and saccharification of a starch substrate. However, there is a need for more efficient means for starch liquefaction, saccharification and fermentation.

SUMMARY OF THE INVENTION

The present invention is directed an enzyme blend composition comprising a glucoamylase (GA), an acid fungal protease (AFP) and an acid stable alpha amylase (AA). Preferably, the ratio of the glucoamylase, an acid stable alpha amylase, and an acid fungal protease is about 1:1.5:0.1 to about 1:8:1, or 1:2:0.2 to 1:5:0.6, as measured by GAU:SSU:SAPU.

The enzyme blend composition is useful for producing end products from fermentable sugars, particularly for producing ethanol from a liquefact. One advantage of the enzyme blend composition is that it results in a greater amount of ethanol relative to the amount of ethanol produced by glucoamylase alone under substantially the same conditions. In one aspect, the increase is greater than 0.5% relative to GA alone, including greater than 1.0%, 1.5%, 2%, and 2.5%.

In one aspect, the GA is obtained from a filamentous fungus selected from the group consisting of: a *Trichoderma* spp., a *Taleromyces* spp., a *Penicillium* spp., an *Aspergillus* spp., and a *Humicola* spp. In a further aspect, the glucoamylase has at least 90% sequence identity with the glucoamylase having the sequence of SEQ ID NO:1, and/or the AFP has at least 90% sequence identity with the AFP having the sequence of SEQ ID NO:14, and/or the alpha amylase has at least 90% sequence identity with the AA having the sequence of SEQ ID NO:5, and/or the alpha amylase has at least 95% sequence identity with the AA having the sequence of SEQ ID NO:5.

The enzyme blend composition optionally includes one or more other enzyme, such as a second glucoamylase, a second alpha amylases, a cellulase, a hemicellulase, a xylanase, a second proteases, a phytase, a pullulanase, a beta amylase, a lipase, a cutinase, a pectinase, a beta-glucanase, a galactosidase, an esterase, a cyclodextrin transglycosyltransferase, and combinations thereof.

The present invention is further directed to method for producing end products such as an alcohol from fermentable sugars. The method comprises the steps of: (a) contacting a slurry comprising a milled grain that contains starch with an alpha amylase to produce a liquefact; (b) contacting the liquefact with a glucoamylase, an acid stable alpha amylase, and an acid fungal protease, to produce fermentable sugars; and (c) fermenting the fermentable sugars in the presence of a fermenting organism to produce end products. In the method, the step (b) saccharification and step (c) fermentation can occur sequentially or occur simultaneously. The glucoamylase, the acid stable alpha amylase, and the acid fungal protease can be added separately to the liquefact. Alternatively, an enzyme blend composition comprising a glucoamylase, an acid stable alpha amylase, and an acid fungal protease is added to the liquefact. Optionally, at least one other enzyme such as, an alpha amylase, a glucoamylase, a phytase, a cellulase, a pullulanase, a protease, or a laccase, is used during the process. The method can also include a step of recovering the end products.

DETAILED DESCRIPTION OF THE INVENTION

Definitions

Figure 1:
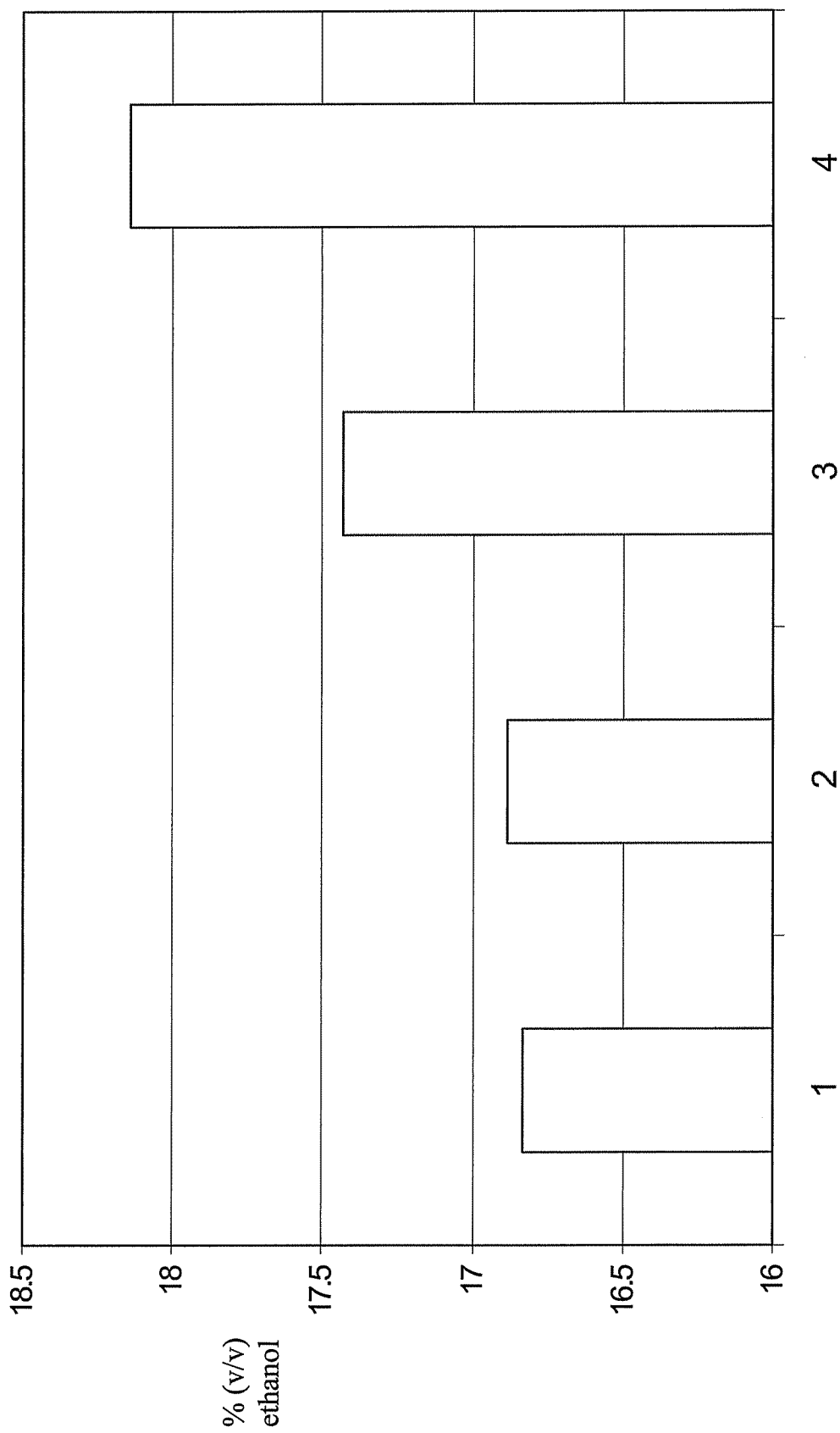
FIG. 1 shows the final alcohol concentrations obtained using different enzyme blends during simultaneous saccharification/fermentation using whole ground corn which has been liquefied as further described in Example 2. The Y-axis is % ethanol (V/V), the X-axis is as follows: 1. TrGA, 0.25 GAU/gds corn, 2. #1+0.05 SAPU AFP/gds corn, 3. #1+2.0 SSU alpha amylase/gds corn, 4. No. 1+0.05 SAPU, AFP+2.0 SSU alpha amylase/gds corn.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

"Alpha amylases" are α-1,4-glucan-4-glucanohydrolases (E.C. 3.2.1.1) and are enzymes that cleave or hydrolyze internal α-1,4-glycosidic linkages in starch (e.g. amylopectin or amylose polymers).

The term "below the gelatinization temperature" refers to a temperature that is less than the gelatinization temperature.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

"Dextrins" are short chain polymers of glucose (e.g., 2 to 10 units).

The term "dry solids (ds)" refers to the total solids of a slurry in % on a dry weight basis.

The term "end product" refers to any carbon-source derived product which is enzymatically converted from a fermentable substrate. In some preferred embodiments, the end product is an alcohol (e.g., ethanol).

As used herein, the term "ethanol producer" or ethanol producing microorganism" refers to a fermenting organism that is capable of producing ethanol from a mono- or oligosaccharide.

The term "fermentable sugars" refers to any sugars that are capable of being fermented by a fermenting organism. Fermentable sugars includes oligosaccharides and dextrins.

A "fermentable sugar" refers to mono- or disaccharides, which may be converted in a fermentation process by a microorganism in contact with the fermentable sugar to produce an end product. In some embodiments, the fermentable sugar is metabolized by the microorganism and in other embodiments the expression and/or secretion of enzymes by the microorganism achieves the desired conversion of the fermentable sugar.

The term "fermentation" refers to the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein, the term "fermenting organism" refers to any microorganism or cell, which is suitable for use in fermentation for directly or indirectly producing an end product.

The term "functional equivalent" means that an enzyme has the same enzymatic functional characteristics of the wild-type enzymes and is derived from a wild-type enzyme.

The term "gelatinization" means solubilization of a starch molecule, generally by cooking, to form a viscous suspension.

The term "gelatinization temperature" refers to the lowest temperature at which gelatinization of a starch containing substrate begins. The exact temperature of gelatinization depends on the specific starch and can vary depending on factors such as plant species and environmental and growth conditions.

The term "granular starch" means raw starch, which is starch that has not been subject to temperatures of gelatinization.

The terms "granular starch hydrolyzing (GSH) enzyme" and "enzymes having granular starch hydrolyzing (GSH) activity" refer to enzymes, which have the ability to hydrolyze starch in granular form.

The term "% homology" is used interchangeably herein with the term "% identity". Exemplary computer programs which can be used to determine identity between two sequences include, but are not limited to, the suite of BLAST programs, e.g., BLASTN, BLASTX, and TBLASTX, BLASTP and TBLASTN, and are publicly available on the Internet (see, for example, the BLAST page on the National Center for Biotechnology Information website). See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A "Liquefact" also called a soluble starch substrate or a liquefied substrate, is a whole ground grain slurry containing a thermostable alpha amylase that has been subjected to high temperature liquefaction resulting in a soluble substrate for saccharification and fermentation or SSF. High temperature is a temperature higher than the gelatinization temperature of the grain.

"Liquefaction" or "liquefy" means a process by which starch is converted to shorter chain and less viscous dextrins.

The term "milled" is used herein to refer to plant material that has been reduced in size, such as by grinding, crushing, fractionating or any other means of particle size reduction. Milling includes dry or wet milling. "Dry milling" refers to the milling of whole dry grain. "Wet milling" refers to a process whereby grain is first soaked (steeped) in water to soften the grain.

The term "oligosaccharides" refers to any compound having 2 to 10 monosaccharide units joined in glycosidic linkages. These short chain polymers of simple sugars include dextrins.

As used herein, "percent (%) sequence identity" with respect to the amino acid or nucleotides sequences identified herein is defined as the percentage of amino acid residues or nucleotides in a candidate sequence that are identical with the amino acid residues or nucleotides in a sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, can be performed without undue experimentation, and calculations of identity values can be obtained with definiteness. See, for example, Ausubel, et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman, et al., (1970) J. Mol. Biol. 48:443; the local homology algorithm of Smith, et al., (1981) Adv. Appl. Math. 2:482; the search for similarity method of Pearson et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see, Altschul, et al., (1990) J. Mol. Biol. 215:403-410). Computerized programs using these algorithms are also available, and include, but are not limited to: ALIGN or Megalign (DNASTAR) software, or WU-BLAST-2 (Altschul, et al., Meth. Enzym., 266:460-480 (1996)); or GAP, BESTFIT, BLAST Altschul, et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum 62 amino acid substitution matrix, with a gap weight of 12 and a length weight of 2. With respect to optimal alignment of two amino acid sequences, the contiguous segment of the variant amino acid sequence can have additional amino acid residues or deleted amino acid residues with respect to the reference amino acid sequence. The contiguous segment used for comparison to the reference amino acid sequence will include at least 20 contiguous amino acid residues and can be 30, 40, 50 or more amino acid residues. Corrections for increased sequence identity associated with inclusion of gaps in the derivative's amino acid sequence can be made by assigning gap penalties.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide can be coded for by more than one nucleotide sequence due to the degeneracy of the genetic code.

Variants of the invention are described by the following nomenclature: [original amino acid residue/position/substituted amino acid residue]. For example the substitution of threonine (T) for alanine (A) at position 89 is represented as A89T. When more than one amino acid is substituted at a given position, the substitution is represented as, for example, 1) A89C, A89D or A89T; 2) A89C, D, or T or c) A89C/D/T. When a position suitable for substitution is identified herein without a specific amino acid suggested, it is to be understood that any amino acid residue can be substituted for the amino acid residue present in the position.

The terms "saccharifying enzyme" and "glucoamylase (E.C. 3.2.1.3)" are used interchangeably herein and refer to any enzyme that is capable of catalyzing the release of D-glucose from the non-reducing ends of starch and related oligo- and polysaccharides.

The phrase "simultaneous saccharification and fermentation (SSF)" refers to a process in the production of end products in which a fermenting organism, such as an ethanol producing microorganism, and at least one enzyme, such as a saccharifying enzyme are combined in the same process step in the same vessel.

The term "slurry" refers to an aqueous mixture comprising insoluble solids, (e.g. granular starch).

As used herein the term "starch" refers to any material comprised of the complex polysaccharide carbohydrates of plants, i.e., amylose and amylopectin with the formula $(C_6H_{10}O_5)_x$, wherein x can be any number.

The term "thin stillage" means the liquid portion of stillage separated from the solids (e.g., by screening or centrifugation) which contains suspended fine particles and dissolved material. The term "backset" is generally used to mean recycled thin stillage.

The term "total sugar content" refers to the total sugar content present in a starch composition.

The term "variant" when used in reference to an enzyme (e.g. an alpha amylase, a glucoamylase, an acid fungal protease, a phytase or the like) means an enzyme derived from a naturally occurring enzyme (wild-type) but having a substitution, insertion or deletion of one or more amino acids as compared to the naturally occurring enzyme. The term includes hybrid forms of the enzyme, wherein for example the enzyme can have a C-terminus derived from one *Bacillus* sp. (e.g., *B. licheniformis*) and an N-terminus derived from a different *Bacillus* sp. (e.g., *B. stearothermophilus*). A variant can have one or more altered properties compared to the wild-type such as but not limited to increased thermal stability, increased proteolytic stability, increase specific activity, broader substrate specificity, broader activity over a pH range or combinations thereof.

The term "wild-type" as used herein refers to an enzyme naturally occurring (native) in a host cell.

Exemplary Embodiments

The inventors have discovered an enzyme blend comprising an alpha amylase, a glucoamylase, and an acid fungal protease. Such composition is useful in a starch conversion process during saccharification and/or saccharification/fermentation. Using such composition provides advantages over using glucoamylase alone in the starch conversion process.

The present invention is directed to a composition comprising a glucoamylase, an acid fungal protease, and an acid stable alpha amylase. The present invention is also directed to the use of the composition to produce desired end products from fermentable sugars, for example, to produce ethanol from a liquefact. One advantage of the composition is that it results in a greater amount of ethanol relative to the amount of ethanol produced by glucoamylase alone under substantially the same conditions. In one aspect, the increase is greater than 0.5% relative to glucoamylase alone, preferably greater than 1.0%, 1.5%, 2%, and 2.5%.

Glucoamylases

Glucoamylase (E.C. 3.2.1.3.) is an enzyme that breaks down starches and dextrins into glucose. Glucoamylase is an exo-acting enzyme; it hydrolyzes alpha 1-4 and alpha 1-6 glucosidic linkages in starch and release glucose.

Glucoamylases useful according to the invention can be a wild-type glucoamylase, a variant or fragment thereof or a hybrid glucoamylase which is derived from, for example, a catalytic domain from one microbial source and a starch binding domain from another microbial source. The following glucoamylases are nonlimiting examples of glucoamylases that can be used in the process encompassed by the invention.

Glucoamylases can be obtained from strains of *Aspergillus niger* G1 and G2 glucoamylase (Boel et al., (1984) EMBO J. 3:1097-1102; WO 92/00381, WO 00/04136 and U.S. Pat. No. 6,352,851); *Aspergillus awamori* glucoamylases (WO 84/02921); *Aspergillus oryzae* glucoamylases (Hata et al., (1991) Agric. Biol. Chem. 55:941-949) and *Aspergillus shirousami*. (See Chen et al., (1996) Prot. Eng. 9:499-505; Chen et al. (1995) Prot. Eng. 8:575-582; and Chen et al., (1994) Biochem J. 302:275-281). *Talaromyces* such as those derived from *T. emersonii, T. leycettanus, T. duponti* and *T. thermophilus* (WO 99/28488; U.S. Pat. No. RE: 32,153; U.S. Pat. No. 4,587,215); strains of *Trichoderma*, such as *T. reesei* and particularly glucoamylases having at least 80%, 85%, 90% and 95% sequence identity to SEQ ID NO: 4 disclosed in US Pat. Pub. No. 2006-0094080; strains of *Rhizopus*, such as *R. niveus* and *R. oryzae*; strains of *Mucor* and strains of *Humicola*, such as *H. grisea* (See, Boel et al., (1984) EMBO J. 3:1097-1102; WO 92/00381; WO 00/04136; Chen et al., (1996) Prot. Eng. 9:499-505; Taylor et al., (1978) Carbohydrate Res. 61:301-308; U.S. Pat. No. 4,514,496; U.S. Pat. No. 4,092,434; U.S. Pat. No. 4,618,579; Jensen et al., (1988) Can. J. Microbiol. 34:218-223 and SEQ ID NO: 3 of WO 2005/052148). In some embodiments, the glucoamylase will have at least 85%, 90%, 92%, 94%, 95%, 96%, 97%, 98% and 99% sequence identity to the amino acid sequence of SEQ ID NO: 3 of WO 05/052148. Other glucoamylases useful in the present invention include those obtained from *Athelia rolfsii* and variants thereof (WO 04/111218).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) J. Biochem. 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Also the enzyme preparation GC480 (Genencor International Inc.) finds use in the invention. The above mentioned glucoamylases and commercial enzymes are not intended to limit the invention but are provided as examples only.

Glucoamylases can be derived from the heterologous or endogenous protein expression of bacteria, plants and fungal sources. Preferred glucoamylases useful in the invention are produced by several strains of filamentous fungi and yeast, in particular, glucoamylases secreted from strains of *Trichoderma*.

Table 1 shows the deduced amino acid sequence (SEQ ID NO: 1) of a *Trichoderma reesei* glucoamylase having 599 amino acids, the catalytic domain (SEQ ID NO: 2) is not underlined and represented by residue positions 1-453; the linker region (SEQ ID NO: 3) is underlined and represented by residue positions 454-491; and the starch binding domain SEQ ID NO: 4 is bold and represented by residue positions 492-599.

TABLE 1

Mature protein sequence of *Trichoderma reesei* glucoamylase (TrGA) (SEQ ID NO: 1)

```
  1 SVDDFISTET PIALNNLLCN VGPDGCRAFG TSAGAVIASP STIDPDYYM

51 WTRDSALVFK NLIDRFTETY DAGLQRRIEQ YITAQVTLQG LSNPSGSLAD

101 GSGLGEPKFE LTLKPFTGNW GRPQRDGPAL RAIALIGYSK WLINNNYQST

151 VSNVIWPIVR NDLNYVAQYW NQTGFDLWEE VNGSSFFTVA NQHRALVEGA

201 TLAATLGQSG SAYSSVAPQV LCFLQRFWVS SGGYVDSNIN TNEGRTGKDV

251 NSVLTSIHTF DPNLGCDAGT FQPCSDKALS NLKVVVDSFR SIYGVNKGIP

301 AGAAVAIGRY AEDVYYNGNP WYLATFAAAE QLYDAIYVWK KTGSITVTAT

351 SLAFFQELVP GVTAGTYSSS SSTFTNIINA VSTYADGFLS EAAKYVPADG

401 SLAEQFDRNS GTPLSALHLT WSYASFLTAT ARRAGIVPPS WANSSASTIP

451 STC*SGASVVG SYSRPTATSF PPSQTPKPGV PSGTPYTPLP C***AIPTSVAVT***

501 *FHELVSTQFG QTKVAGNAA ALGNWSTSAA VALDAVNYAD NHPLWIGTVN*

551 *LEAGDVVEYK YINVGQDGSV TWESDPNHTY TVPAVACVTQ VVKEDTWQS*
```

The inventors have identified two domains responsible for glucoamylase activity, i.e., a binding domain and catalytic domain. Conservative mutations in these domains are likely to result in a protein having glucoamylase activity. Although all conservative amino acid substitutions in these domains do not necessarily result in a protein having glucoamylase activity, those of ordinary skill in the art would expect that many of these conservative substitutions would result in a protein having the glucoamylase activity. Further, amino acid substitutions outside of the two identified functional domains are unlikely to greatly affect the glucoamylase activity.

In some embodiments, the glucoamylase useful in the invention has at least 85%, 90%, 92%, 94%, 95%, 96%, 97%, 98% or 99% sequence identity to the amino acid sequence of SEQ ID NO: 1 or 2.

Alpha Amylases

Alpha amylases useful according to the invention can be a wild-type alpha amylase, a variant or fragment thereof or a hybrid alpha amylase which is derived from for example a catalytic domain from one microbial source and a starch binding domain from another microbial source. Alternatively, the alpha amylase can be a variant that has been engineered to be acid stable. The alpha amylase can also be an alpha amylase having granular starch hydrolyzing activity (GSHE) because the enzymes act to break down more of the starch in the liquefact.

Examples of fungal alpha amylases include those obtained from filamentous fungal strains including but not limited to strains of *Aspergillus* (e.g., *A. niger*, *A. kawachi*, and *A. oryzae*); *Trichoderma* sp., *Rhizopus* sp., *Mucor* sp., and *Penicillium* sp. In some embodiments, the alpha amylase is obtained from a strain of *Aspergillus kawachi* or a strain of *Trichoderma reesei*.

Commercially available alpha amylases contemplated for use in the compositions and method encompassed by the invention include: GZYME 997; and CLARASE L (Genencor International Inc.); TERMAMYL 120-L, LC and SC and SUPRA (Novozymes Biotech); SAN SUPER (Novozymes A/S) and FUELZYME FL (Diversa/Valley Research).

In some preferred embodiments, the alpha amylase useful in the invention is an acid stable alpha amylase which, when added in an effective amount, has activity in the pH range of 3.0 to 7.0 and preferably in the pH range from 3.5 to 6.5, including activity at a pH of about 4.0, 4.5, 5.0, 5.5, and 6.0. Acid stable alpha amylases useful according to the invention can be fungal alpha amylase or bacterial alpha amylases. Preferred acid stable alpha amylases include those obtained from *Aspergillus kawachi* (e.g., AkAA), *Aspergillus niger* (e.g., AnAA), and *Trichoderma reesei* (e.g., TrAA).

Table 2 shows the mature protein sequence for *Aspergillus kawachi* alpha amylase (AkAA)(SEQ ID NO:5). The putative linker is TTTTTTAATSTSKATTSSSSSSAAATTSS SCTAT STT (SEQ ID NO: 6), underlined. The amino acids upstream of the linker comprise the catalytic domain (SEQ ID NO: 7), not underlined. The amino acids downstream of the linker comprise the starch binding domain (SBD), (SEQ ID NO: 8), bold. The SBD includes the last 102 amino acids of the polypeptide.

TABLE 2

Mature protein sequence of *Aspergillus kawachi* alpha amylase (AkAA) (SEQ ID NO: 5)

LSAAEWRTQSIYFLLTDRFGRTDNSTTATCNTGDQIYCGGSWQGIINHLDYIQGMGFTAIWI

SPITEQLPQDTSDGEAYHGYWQQKIYNVNSNFGTADDLKSLSDALHARGMYLMVDVVPNHMG

YAGNGNDVDYSVFDPFDSSSYFHPYCLITDWDNLTMVQDCWEGDTIVSLPDLNTTETAVRTI

WYDWVADLVSNYSVDGLRIDSVEEVEPDFFPGYQEAAGVYCVGEVDNGNPALDCPYQKYLDG

VLNYPIYWQLLYAFESSSGSISNLYNMIKSVASDCSDPTLLGNFIENHDNPRFASYTSDYSQ

AKNVLSYIFLSDGIPIVYAGEEQHYSGGDVPYNREATWLSGYDTSAELYTWIATTNAIRKLA

ISADSDYITYANDPIYTDSNTIAMRKGTSGSQIITVLSNKGSSGSSYTLTLSGSGYTSGTKL

IEAYTCTSVTVDSNGDIPVPMASGLPRVLLPASVVDSSSLCGGSGN*TTTTTTAATSTSKATT*

*SSSSSSAAATTSSSCTATSTT*LPITFEELVTTTYGEEVYLSGSISQLGEWDTSDAVKLSADD

YTSSNPEWSVTVSLPVGTTFEYKFIKVDEGGSVTWESDPNREYTVPECGSGSGETVVDTWR

The inventors have identified two domains responsible for alpha amylase activity, i.e., a binding domain and catalytic domain. Conservative mutations in these domains are likely to result in a protein having alpha amylase activity. Although all conservative amino acid substitutions in these domains do not necessarily result in a protein having alpha amylase activity, those of ordinary skill in the art would expect that many of these conservative substitutions would result in a protein having the alpha amylase activity. Further, amino acid substitutions outside of the two identified functional domains are unlikely to greatly affect the alpha amylase activity.

In some embodiments, the alpha amylase has at least 85%, 90%, 92%, 94%, 95%, 96%, 97%, 98%, or 99% sequence identity to the amino acid sequence of SEQ ID NO: 5 or 7.

Table 3 shows the mature protein sequence of an *Aspergillus niger* alpha amylase (AnAA) (SEQ ID NO: 9). In the table, the catalytic domain is represented by amino acids 1-478 (SEQ ID NO: 10), not underlined. The linker region is underlined (SEQ ID NO: 11). The starch-binding domain is bold (SEQ ID NO: 12).

TABLE 3

Mature protein sequence of *Aspergillus niger* alpha amylase AnAA (SEQ ID NO: 9)

LSAAEWRTQSIYFLLTDRFGRTDNSTTATCNTGDQIYCGGSWQGIINHLDYIQGMGFTAIWI

SPITEQLPQDTADGEAYHGYWQQKIYDVNSNFGTADDLKSLSDALHARGMYLMVDVVPNHMG

YAGNGNDVDYSVFDPFDSSSYFHPYCLITDWDNLTMVQDCWEGDTIVSLPDLNTTETAVRTI

WYDWVADLVSNYSVDGLRIDSVLEVEPDFFPGYQEAAGVYCVGEVDNGNPALDCPYQEYLDG

VLNYPIYWQLLYAFESSSGSISDLYNMIKSVASDCSDPTLLGNFIENHDNPRFASYTSDYSQ

AKNVLSYIFLSDGIPIVYAGEEQHYSGGKVPYNREATWLSGYDTSAELYTWIATTNAIRKLA

ISADSAYITYANDAFYTDSNTIAMRKGTSGSQVITVLSNKGSSGSSYTLTLSGSGYTSGTKL

IEAYTCTSVTVDSSGDIPVPMASGLPRVLLPASVVDSSSLCGGS<u>GSNSSTTTTTATSSSTA</u>

<u>TSKSASTSSTSTA</u>CTATSTSLAVTFEELVTTTYGEEIYLSGSISQLGDWDTSDAVKMSADDY

TSSNPEWSVTVTLPVGTTFEYKFIKVESDGTVTWESDPNREYTVPECGSGETVVDTWR

In some embodiments, the alpha amylase has at least 85%, 90%, 92%, 94%, 95%, 96%, 97%, 98%, or 99% sequence identity to the amino acid sequence of SEQ ID NO: 9 or 10.

Table 4 gives the mature protein sequence for the *Trichoderma* alpha amylase (TrAA) having 443 amino acids (SEQ ID NO:13). This alpha amylase does not contain an SBD or a linker.

TABLE 4

Mature protein sequence of *Trichoderma reesei* alpha amylase (TrAA) (443 amino acids) (SEQ ID NO: 13)

| | | | |
|---|---|---|---|
| DTAAWRSRTI | YFALTDRIAR | GSGDTGGSAC | GNLGDYCGGT |
| FQGLESKLDY | IKGMGFDAIW | ITPVVTSDDG | GYHGYWAEDI |
| DSINSHYGSA | DDLKSLVNAA | HSKGFYMMVD | VVANHMGYAN |
| ISDDSPSPLN | QASSYHPECD | IDYNNQTSVE | NCWISGLPDL |
| NTQSSTIRSL | YQDWVSNLVS | TYGFDGVRID | TVKHVEQDYW |
| PGFVNATGVY | CIGEVFDGDP | NYLLPYASLM | PGLLNYAIYY |
| PMTRFFLQQG | SSQDMVNMHD | QIGSMFPDPT | ALGTFVDNHD |
| NPRFLSIKND | TALLKNALTY | TILSRGIPIV | YYGTEQAFSG |
| GNDPANREDL | WRSGFNAQSD | MYDAISKLTY | AKHAVGGLAD |
| NDHKHLYVAD | TAYAFSRAGG | NMVALTTNSG | SGSSAQHCFG |
| TQVPNGRWQN | VFDEGNGPTY | SADGNGQLCL | NVSNGQPIVL |
| LSS | | | |

In some embodiments, the alpha amylase useful in the invention has at least 85%, 90%, 92%, 94%, 95%, 96%, 97%, 98%, or 99% sequence identity to the amino acid sequence of SEQ ID NO: 13.

Acid Fungal Proteases

An acid fungal protease (AFP) useful according to the invention can be a wild-type acid fungal protease, a variant or fragment thereof, or a genetically engineered mutant AFP.

Acid fungal proteases include for example, those obtained from *Aspergillus*, *Trichoderma*, *Mucor* and *Rhizopus*, such as *A. niger*, *A. awamori*, *A. oryzae* and *M. miehei*. AFP can be derived from heterologous or endogenous protein expression of bacteria, plants and fungi sources. In particular, AFP secreted from strains of *Trichoderma* are preferred.

Table 5 shows the mature protein sequence (355 amino acids) (SEQ ID NO: 14) for a preferred AFP from *Trichoderma reesei*.

TABLE 5

Mature protein sequence of *Trichoderma reesei* acid fungal protease (AFP) (SEQ ID NO: 14):

KYGAPISDNLKSLVAARQAKQALAKRQTGSAPNHPSDSADSEYITSVSIGTPAQVLPLDFDT

GSSDLWVFSSETPKSSATGHAIYTPSKSSTSKKVSGASWSISYGDGSSSSGDVYTDKVTIGG

FSVNTQGVESATRVSTEFVQDTVISGLVGLAFDSGNQVRPHPQKTWFSNAASSLAEPLFTAD

LRHGQNGSYNFGYIDTSVAKGPVAYTPVDNSQGFWEFTASGYSVGGGKLNRNSIDGIADTGT

TLLLLDDNVVDAYYANVQSAQYDNQQEGVVFDCDEDLPSFSFGVGSSTITIPGDLLNLTPLE

EGSSTCFGGLQSSSGIGINIFGDVALKAALVVFDLGNERLGWAQK

In some embodiments, the acid fungal protease useful in the invention has at least 85%, 90%, 92%, 94%, 95%, 96%, 97%, 98%, or 99% sequence identity to the amino acid sequence of SEQ ID NO:14.

Secondary Enzymes

While some embodiments of the invention include a composition comprising at least one acid stable alpha-amylase, at least one glucoamylase and at least one acid fungal protease, the composition can optionally include other enzymes. For example, when the compositions are used in various applications (e.g. starch processing applications), further secondary enzymes can be included. The blend composition according to the invention can be used in the saccharification step and/or the fermenting step along with the fermenting microorganism and other components and other secondary enzymes. The additional enzymes include without limitation: additional glucoamylases, additional alpha amylases, additional proteases, cellulases, hemicellulases, xylanase, phytases, pullulanases, lipases, cutinases, pectinases, beta-glucanases, galactosidases, esterases, cyclodextrin transglycosyltransferases (CGTases), beta-amylases and combinations thereof.

In some embodiments, the additional enzyme is a second acid stable alpha amylase such as a fungal alpha amylase. In some embodiments, the second alpha amylase is a GSHE, such as AkAA, TrAA or AsAA. Non-limiting examples of other alpha amylases that can be useful in combination with the blend are those derived from *Bacillus, Aspergillus, Trichoderma, Rhizopus, Fusarium, Penicillium, Neurospora* and *Humicola*.

Some of these amylases are commercially available e.g., TERMAMYL and SUPRA available from Novo Nordisk A/S, FUELZYME FL from Diversa, LIQUEZYME SC from Novo Nordisk A/S and SPEZYME FRED, SPEZYME ETHYL and GZYME G997 available from Genencor International, Inc.

In another embodiment, the invention can include the addition of a phytase. A phytase is an enzyme that is capable of liberating at least one inorganic phosphate from an inositol hexaphosphate. Phytases are grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase. Phytases can be obtained from microorganisms such as fungal and bacterial organisms. Some of these microorganisms include e.g. *Aspergillus* (e.g., *A. niger, A. terreus*, and *A. fumigatus*), *Myceliophthora* (*M. thermophila*), *Talaromyces* (*T. thermophilus*) *Trichoderma* spp (*T. reesei*). and *Thermomyces* (WO 99/49740). Also phytases are available from *Penicillium* species, e.g., *P. hordei* (ATCC No. 22053), *P. piceum* (ATCC No. 10519), or *P. brevi-compactum* (ATCC No. 48944). See, for example U.S. Pat. No. 6,475, 762. In addition, phytases are available from *Peniophora, E. coli, Citrobacter, Enterbacter* and *Buttiauxella* (see WO2006/043178, filed Oct. 17, 2005). Commercial phytases are available such as NATUPHOS (BASF), RONOZYME P (Novozymes A/S), PHZYME (Danisco A/S, Diversa) and FINASE (AB Enzymes). In some preferred embodiments, the phytase useful in the present invention is one derived from the bacterium *Buttiauxella* spp. The *Buttiauxella* spp. includes *B. agrestis, B. brennerae, B. ferragutiase, B. gaviniae, B. izardii, B. noackiae*, and *B. warmboldiae*. Strains of *Buttiauxella* species are available from DSMZ, the German National Resource Center for Biological Material (Inhoffenstrabe 7B, 38124 Braunschweig, Germany). *Buttiauxella* sp. strain P1-29 deposited under accession number NCIMB 41248 is an example of a particularly useful strain from which a phytase can be obtained and used according to the invention.

Cellulases can also be used with the blends and/or compositions according to the invention. Cellulases are enzyme compositions that hydrolyze cellulose ($\beta$-1,4-D-glucan linkages) and/or derivatives thereof, such as phosphoric acid swollen cellulose. Cellulases include the classification of exo-cellobiohydrolases (CBH), endoglucanases (EG) and $\beta$-glucosidases (BG) (EC3.2.191, EC3.2.1.4 and EC3.2.1.21). Examples of cellulases include cellulases from *Penicillium, Trichoderma, Humicola, Fusarium, Thermomonospora, Cellulomonas, Clostridium* and *Aspergillus*. Commercially available cellulases sold for feed applications are beta-glucanases such as ROVABIO (Adisseo), NATUGRAIN (BASF), MULTIFECT BGL (Danisco Genencor) and ECONASE (AB Enzymes).

Xylanases can also be used with the blends and/or compositions according to the invention. Xylanases (e.g. endo-$\beta$-xylanases (E.C. 3.2.1.8), which hydrolyze the xylan backbone chain can be from bacterial sources, such as *Bacillus, Streptomyces, Clostridium, Acidothermus, Microtetrapsora* or *Thermonospora*. In addition xylanases can be from fungal sources, such as *Aspergillus, Trichoderma, Neurospora, Humicola, Penicillium* or *Fusarium*. (See, for example, EP473 545; U.S. Pat. No. 5,612,055; WO 92/06209; and WO 97/20920). Commercial preparations include MULTIFECT and FEEDTREAT Y5 (Danisco Genencor), RONOZYME WX (Novozymes A/S) and NATUGRAIN WHEAT (BASF).

Additional proteases can also be used with the blends and/or compositions according to the invention. Proteases can be derived from bacterial or fungal sources. Sources of bacterial proteases include proteases from *Bacillus* such as *B. amyloliquefaciens, B. lentus, B. licheniformis*, and *B. subtilis*. These sources include subtilisin such as a subtilisin obtainable from *B. amyloliquefaciens* and mutants thereof (U.S. Pat. No. 4,760,025). Suitable commercial protease includes MULTIFECT P 3000 (Danisco Genencor) and SUMIZYME FP (Shin Nihon). Sources of fungal proteases include *Trichoderma* (for example NSP-24), *Aspergillus, Humicola* and *Penicillium*, for example.

Enzyme Blend Composition

The enzyme blend compositions of the invention comprise a glucoamylase, an alpha amylase, and an acid fungal protease. The three enzyme components can be used as a blended formulation comprising three enzyme components mixed together, or the enzyme components can be individually added during a process step to result in a composition encompassed by the invention. Preferably, the composition of the invention is used during a step in starch conversion such that an activity ratio as defined below is maintained. This may involve adding the separate components of the composition in a time-wise manner such that the ratio is maintained, for example adding the components simultaneously.

In some embodiments, the enzyme blend compositions include:

a) a GA having at least 95% or at least 97% sequence identity to SEQ ID NO:1, an AkAA having at least 97% sequence identity to SEQ ID NO:5 and an AFP;

b) a GA having at least 95% or at least 97% sequence identity to SEQ ID NO:1, an acid stable AA, and an AFP;

c) a GA having at least 95% or at least 97% sequence identity to SEQ ID NO:1, a GSHE AA, and an AFP having at least 90%, 95%, or 99% sequence identity to SEQ ID NO:14);

d) a GA, AkAA or TrAA, and an acid fungal protease having at least 95% or at least 97% sequence identity to SEQ ID NO:14;

e) a GA, AkAA, and an acid fungal protease having at least 95% or at least 97% sequence identity to SEQ ID NO:14;

f) a GA having at least 95% or at least 97% sequence identity to SEQ ID NO:1, AkAA, and an AFP having at least 95% or at least 97% sequence identity to SEQ ID NO:14;

g) a GA having at least 95% or at least 97% sequence identity to SEQ ID NO:1, TrAA, and an acid fungal protease having at least 95% or at least 97% sequence identity to SEQ ID NO:14;

h) a GA having at least 95% sequence identity to the sequence of SEQ ID NO:1, an AFP having at least 95% sequence identity to the sequence of SEQ ID NO:14, and an AA having at least 95% sequence identity to the sequence of SEQ ID NO:5;

i) a GA having at least 98% sequence identity to the sequence of SEQ ID NO:1, an AFP having at least 98% sequence identity to the sequence of SEQ ID NO:14, and an AA having at least 98% sequence identity to the sequence of SEQ ID NO:5; and j) STARGEN™ 001, which is a blend of an acid stable *Aspergillus kawachi* alpha amylase, an *Aspergillus niger* glucoamylase (available commercially from Genencor International, Inc), and an acid fungal protease.

The enzyme activities are often measured in GAU for glucoamylases, SSU for alpha amylases, and SAPU for acid fungal proteases.

In some embodiments, the enzyme activity ratios are defined below, where the ratio of each enzyme is shown in reference to glucoamylase (GA). For example, the ratio of GA (GAU) to AA (SSU) is from about 1:1 to 1:15, including but not limited to: 1:2, 1:3, 1:4, 1:5, 1:6, 1:7, 1:8, 1:9, and 1:10. The ratio can be as low as 1:1 and as high as 1:15. In preferred embodiments, the ratio of GA (GAU) to AA (SSU) is from about 1:1.5 to about 1:8 or from about 1:2 to about 1:5. In one preferred embodiment, the ratio of GA (GAU) to AA (SSU) is 1:4.

In some embodiments, the ratio of GA (GAU) to AFP (SAPU) is from about 1:0.1 to about 1:5, including but not limited to: 1:0.2, 1:0.3, 1:0.4, 1:0.5, 1:0.6, 1:0.7, 1:0.8, 1:0.9, 1:1 or as high as 1:5, including 1:2, 1:3, and 1:4. Preferably, the ratio of GA (GAU) to AFP (SAPU) is between about 1:0.1 to 1:1, or 1:0.2 to 1:0.8, or 1:0.2 to 1:0.6. In one preferred embodiment, the ratio of GA (GAU) to AFP (SAPU) is about 1:0.4.

In one preferred composition, the ratio of the glucoamylase, the acid stable alpha amylase, and the acid fungal protease is about 1:1.5:0.1 to about 1:8:1, as measured by GAU:SSU:SAPU.

In another preferred composition, the ratio of the glucoamylase, the acid stable alpha amylase, and the acid fungal protease is about 1:2:0.2 to 1:5:0.6, as measured by GAU:SSU:SAPU.

In one preferred composition, the ratio of GA:AA:AFP is about 1:4:0.4. As used herein regarding the activity ratio, "about" is meant to include ±15% of the recited value.

Methods of Use

The present invention is further directed to a method for producing end products from fermentable sugars. The method comprises the steps of: (a) contacting a slurry comprising a milled grain that contains starch with an alpha amylase to produce a liquefact; (b) contacting the liquefact with a glucoamylase, an acid stable alpha amylase, and an acid fungal protease, to produce fermentable sugars; and (c) fermenting the fermentable sugars in the presence of a fermenting organism to produce end products. In the method, the step (b) saccharification and step (c) fermentation can occur sequentially or occur simultaneously. The glucoamylase, the acid stable alpha amylase, and the acid fungal protease can be added separately to the liquefact. Alternatively, an enzyme blend composition comprising a glucoamylase, an acid stable alpha amylase, and an acid fungal protease can be added to the liquefact. Each step is detailed in details below.

Starch Conversion

A substrate comprising plant material is reduced or milled by methods known in the art. Plant material can be obtained from: wheat, corn, rye, sorghum (milo), rice, millet, barley, triticale, cassava (tapioca), potato, sweet potato, sugar beets, sugarcane, and legumes such as soybean and peas. Preferred plant material includes corn, barley, wheat, rice, milo and combinations thereof. Plant material can include hybrid varieties and genetically modified varieties (e.g. transgenic corn, barley or soybeans comprising heterologous genes).

Any part of the plant containing starch can be used to produce the liquefact, including but not limited to, plant parts such as leaves, stems, hulls, husks, tubers, cobs, grains and the like. Preferred whole grains include corn, wheat, rye, barley, sorghum and combinations thereof. In other embodiments, starch can be obtained from fractionated cereal grains including fiber, endosperm and/or germ components. Methods for fractionating plant material, such as corn and wheat, are known in the art. In some embodiments, plant material obtained from different sources can be mixed together (e.g. corn and milo or corn and barley). Methods of milling are well known in the art and reference is made to THE ALCOHOL TEXTBOOK: A REFERENCE FOR THE BEVERAGE, FUEL AND INDUSTRIAL ALCOHOL INDUSTRIES $3^{rd}$ ED. K. A. Jacques et al., Eds, (1999) Nottingham University Press. See, Chapters 2 and 4.

In some embodiments, the plant material, whether reduced by milling or other means, will be combined with a solution resulting in a slurry comprising starch substrate. In some embodiments, the slurry can include a side stream from starch processing such as backset. In some embodiments, the slurry will comprise 15-55% ds (e.g., 20-50%, 25-45%, 25-40%, and 20-35%). The slurry comprising the reduced plant material can be subject to a liquefaction process wherein an alpha amylase can be added during the liquefaction step. This results in a liquefact. To produce the liquefact, a single or split dose of an alpha amylase can be added to the slurry. One skilled in the art can readily determine the effective dosage of alpha amylase to be used in the liquefaction processes.

In some embodiments, the amount of alpha amylase used for liquefaction is an amount effective to cause liquefaction of a majority of the starch. In other embodiments, the amount is effective to enable liquefaction of greater than 40% of the starch, including 50%, 60%, 70%, 80%, 90%, and 100%. In some embodiments, the range will be 0.05 to 50 AAU/gds, also 0.1 to 20 AAU/gds and also 1.0 to 10 AAU/gds. In further embodiments, the alpha amylase dosage will be in the range of 0.01 to 10.0 kg/metric ton (MT) ds; also 0.05 to 5.0 kg/MT ds; and also 0.1 to 4.0 kg/MT ds.

In some embodiments, the alpha amylase is added at a temperature of 0 to 30° C. below the starch gelatinization temperature of the granular starch of the reduced plant material. This temperature can be 0 to 25° C., 0 to 20° C., 0 to 15° C. and 0 to 10° C. below the starch gelatinization temperature. This specific value will vary and depends on the type of grain comprising the slurry. For example, the starch gelatinization temperature of corn is generally higher than the starch gelatinization temperature of rye or wheat. In some embodiments, the temperature will be between 45 to 80° C., also between 50 to 75° C., also between 50 to 72° C. and in some embodiments the temperature will be below 68° C.; below 65° C., below 62° C., below 60° C. and also below 55° C. In other embodiments the temperature will be above 40° C., above 45° C., above 50°

C., and above 55° C. In some preferred embodiments, the temperature of the incubation will be between 58 to 72° C. and also between 60 to 68° C.

In some embodiments, the slurry will be maintained at a pH range of about 3.0 to less than 6.5, also at a pH range of 4.0 to less than 6.2, also at a pH range of about 4.5 to less than 6.0 and preferably at a pH range of about 5.0 to 6.0 (e.g. about 5.4 to 5.8), and the milled grain in the slurry will be contacted with the enzyme composition for a period of time of 2 minutes to 8 hours (e.g., 5 mins to 3 hrs; 15 mins to 2.5 hrs and 30 min to 2 hrs). In a further step the incubated substrate will be liquefied by exposing the incubated substrate to an increase in temperature such as 0 to 55° C. above the starch gelatinization temperature. (e.g. to 65° C. to 120° C., 70° C. to 110° C., 70° C. to 90° C.) for a period of time of 2 minutes to 8 hours (e.g., 2 minutes to 6 hrs, 5 minutes to 4 hours and preferably 1 hr to 2 hrs) at a pH of about 4.0 to 6.5. In some embodiments, the temperature can be raised to a temperature to between about 85-90° C. and a single does of alpha amylase can be used. If the temperature is raised above 90-105° C., a second dose of alpha amylase can be added after the temperature returns to normal. In a further embodiment, the temperature can be raised to between about 105 and 140° C. and a split dose of alpha amylase can be used with one part being added before raising the temperature and the other part added after the temperature has been brought down to at least below 105° C., including below 104, 103, 102, 101, 100, 99, 98, 97, 96, 95, 94, 93, 92, and 91° C., but preferably below 90° C. In some embodiments, the resulting liquefact is cooled before saccharification.

Saccharification and Fermentation

The liquefact obtained above can be contacted with a glucoamylase, an acid stable alpha amylase, and an acid fungal protease in a single dose or a split dose as long as a desired ratio of enzymes is maintained. Thus, a split dose means that the total dose in desired ratio is added in more than one portion, including two portions or three portions. In one embodiment, one portion of the total dose is added at the beginning and a second portion is added at a specified time in the process. In one embodiment, at least a portion of the dose is added at the beginning of the saccharification (or SSF) to begin the saccharification process. In one embodiment, each enzyme in the enzyme composition can be added to the liquefact separately, but simultaneously or close enough in time such that the activity ratio is maintained. Alternatively, the enzyme blend composition comprising a glucoamylase, an acid stable alpha amylase, and an acid fungal protease can be added during one or both of the saccharification and fermentation. The ratio of the glucoamylase, an acid stable alpha amylase, and an acid fungal protease is preferably about 1:1.5:0.1 to about 1:8:1, and more preferably about 1:2:0.2 to 1:5:0.6, as measured by GAU:SSU:SAPU.

The saccharification process can last for 12 to 120 hours. However, it is common to perform a saccharification for 30 minutes to 2 hours and then complete the saccharification during fermentation. Sometimes this is referred to as simultaneous saccharification and fermentation (SSF). Saccharification is commonly carried out at temperatures of 30 to 65° C. and typically at pH of 3.0 to 5.0, including 4.0 to 5.0. The saccharification can result in the production of fermentable sugars.

In some embodiments the fermentable sugars are subjected to fermentation with fermenting microorganisms. The contacting step and the fermenting step can be performed simultaneously in the same reaction vessel or sequentially. In general, fermentation processes are described in The Alcohol Textbook 3$^{rd}$ ED, A Reference for the Beverage, Fuel and Industrial Alcohol Industries, Eds Jacques et al., (1999) Nottingham University Press, UK.

In some embodiments, the method further comprises using the fermentable sugars (dextrin e.g. glucose) as a fermentation feedstock in microbial fermentations under suitable fermentation conditions to obtain end-products, such as alcohol (e.g., ethanol), organic acids (e.g., succinic acid, lactic acid), sugar alcohols (e.g., glycerol), ascorbic acid intermediates (e.g., gluconate, DKG, KLG) amino acids (e.g., lysine), proteins (e.g., antibodies and fragment thereof).

In some preferred embodiments, the fermentable sugars are fermented with a yeast at temperatures in the range of 15 to 40° C., 20 to 38° C., and also 25 to 35° C.; at a pH range of pH 3.0 to 6.5; also pH 3.0 to 6.0; pH 3.0 to 5.5, pH 3.5 to 5.0 and also pH 3.5 to 4.5 for a period of time of 5 hrs to 120 hours, preferably 12 to 120 and more preferably from 24 to 90 hours to produce an alcohol product, preferably ethanol.

Yeast cells are generally supplied in amounts of $10^4$ to $10^{12}$, and preferably from $10^7$ to $10^{10}$ viable yeast count per ml of fermentation broth. The fermentation will include in addition to a fermenting microorganisms (e.g. yeast) nutrients, optionally acid and additional enzymes. In some embodiments, in addition to the raw materials described above, fermentation media will contain supplements including but not limited to vitamins (e.g. biotin, folic acid, nicotinic acid, riboflavin), cofactors, and macro and micro-nutrients and salts (e.g. $(NH4)_2SO_4$; $K_2HPO_4$; $NaCl$; $MgSO_4$; $H_3BO_3$; $ZnCl_2$; and $CaCl_2$).

In some preferred embodiments, the milled plant material includes barley, milo, corn and combinations thereof, and the contacting and fermenting steps are conducted simultaneously at a pH range of 3.5 to 5.5, a temperature range of 30-45° C., and for a period of time of 48 to 90 hrs, wherein at least 50% of the starch is solubilized.

End Products

One preferred end product of the instant fermentation process is an alcohol product, e.g. ethanol. In further embodiments, the end products are the fermentation co-products such as distillers dried grains (DDG) and distiller's dried grain plus solubles (DDGS), which can be used as an animal feed.

In further embodiments, by use of appropriate fermenting microorganisms as known in the art, the fermentation end products can include without limitation glycerol, 1,3-propanediol, gluconate, 2-keto-D-gluconate, 2,5-diketo-D-gluconate, 2-keto-L-gulonic acid, succinic acid, lactic acid, amino acids and derivatives thereof.

Fermenting Organisms

Examples of fermenting organisms are ethanologenic microorganisms or ethanol producing microorganisms such as ethanologenic bacteria which express alcohol dehydrogenase and pyruvate dehydrogenase and which can be obtained from *Zymomonas moblis* (See e.g. U.S. Pat. No. 5,000,000; U.S. Pat. No. 5,028,539, U.S. Pat. No. 5,424,202; U.S. Pat. No. 5,514,583 and U.S. Pat. No. 5,554,520). In additional embodiments, the ethanologenic microorganisms express xylose reductase and xylitol dehydrogenase, enzymes that convert xylose to xylulose. In further embodiments, xylose isomerase is used to convert xylose to xylulose. In particularly preferred embodiments, a microorganism capable of fermenting both pentoses and hexoses to ethanol are utilized. For example, in some embodiments the microorganism can be a natural or non-genetically engineered microorganism or in other embodiments the microorganism can be a recombinant microorganism.

The fermenting microorganisms include, but not limited to, bacterial strains from *Bacillus, Lactobacillus, E. coli,*

*Erwinia, Pantoea* (e.g., *P. citrea*), *Pseudomonas* and *Klebsiella* (e.g. *K. oxytoca*). (See e.g. U.S. Pat. No. 5,028,539, U.S. Pat. No. 5,424,202 and WO 95/13362). *Bacillus* is a preferred fermenting microorganism. The fermenting microorganism used in the fermenting step will depend on the end product to be produced.

In another preferred embodiments, the ethanol-producing microorganism is a fungal microorganism, such as *Trichoderma*, a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China).

For example, when lactic acid is the desired end product, a *Lactobacillus* sp. (*L. casei*) can be used; when glycerol or 1,3-propanediol are the desired end-products, *E. coli* can be used; and when 2-keto-D-gluconate, 2,5-diketo-D-gluconate, and 2-keto-L-gulonic acid are the desired end products, *Pantoea citrea* can be used as the fermenting microorganism. The above enumerated list are only examples and one skilled in the art will be aware of a number of fermenting microorganisms that can be appropriately used to obtain a desired end product.

Recovery of End Products

The end product produced according to the process can be separated and/or purified from the fermentation media. Methods for separation and purification are known, for example by subjecting the media to extraction, distillation and column chromatography. In some embodiments, the end product is identified directly by submitting the media to high-pressure liquid chromatography (HPLC) analysis.

In further embodiments, the mash can be separated by, for example, centrifugation into the liquid phase and solids phase and end products such as alcohol and solids recovered. The alcohol can be recovered by means such as distillation and molecular sieve dehydration or ultra filtration.

In some embodiments, use of an enzyme blend or composition according to the invention in a method of ethanol production will result in a yield of ethanol that is greater than 8%, 10%, 12%, 14%, 16%, 17%, 18%, 19%, 20%, 21%, and 22% (v/v).

Optionally following fermentation, alcohol (e.g. ethanol) can be extracted by for example distillation. Ethanol can be used for fuel, portable or industrial ethanol.

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

In the disclosure and experimental section which follows, the following abbreviations apply: wt % (weight percent); ° C. (degrees Centigrade); $H_2O$ (water); $dH_2O$ (deionized water); $dIH_2O$ (deionized water, Milli-Q filtration); g or gm (grams); μg (micrograms); mg (milligrams); kg (kilograms); μl (microliters); mL and ml (milliliters); mm (millimeters); μm (micrometer); M (molar); mM (millimolar); μM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); IKA (IKA Works Inc. 2635 North Chase Parkway SE, Wilmington, N.C.); Genencor (Genencor International, Inc., Palo Alto, Calif.); Ncm (Newton centimeter) and ETOH (ethanol). eq (equivalents); N (Normal); ds or DS (dry solids content), SAPU (spectrophotometric acid protease unit, wherein in 1 SAPU is the amount of protease enzyme activity that liberates one micromole of tyrosine per minute from a casein substrate under conditions of the assay) and GAU (glucoamylase unit, which is defined as the amount of enzyme that will produce 1 g of reducing sugar calculated as glucose per hour from a soluble starch substrate at pH 4.2 and 60° C.).

Materials and Methods

Viscosity Measurements

A glass cooker-viscometer, LR-2.ST system IKA was used to determine viscosity. In brief the viscometer consists of a 2000 ml double walled glass vessel with an anchor mixer that is stirred by a Eurostar Labortechnik power control-viscometer (the viscosity range of the Viscoklick viscometer is 0-600 Ncm. In general for the examples described herein a slurry comprising starch substrate and an appropriate amount of enzyme was poured into the viscometer vessel. The temperature and viscosity were recorded during heating to 85° C. and incubation was continued for additional 60 to 120 mins. Viscosity measured as Ncm was recorded at intervals.

Enzymes

The glucoamylase used was the *Trichoderma reesei* GA (TrGA) shown as SEQ ID NO:1 in Table 1 (see also US 2006/0003408, published Jan. 5, 2006 and US 2006/0094080, published May 4, 2006, both of which are incorporated by reference). The acid fungal protease used in the examples was a *Trichoderma reesei* protein having the sequence of SEQ ID NO:14 (see also US 2006/015342, published Jul. 13, 2006, SEQ ID NO:10, incorporated by reference), the alpha amylase used was the *Aspergillus kawachi* alpha amylase (AkAA) shown herein as SEQ ID NO:5, (U.S. Pat. No. 7,205,138). All of the patent applications are herein incorporated by reference in their entirety.

Carbohydrate Analysis by High Pressure Liquid Chromatographic (HPLC): The composition of the reaction products of oligosaccharides was measured by HPLC (Beckman System Gold 32 Karat Fullerton, Calif. equipped with a HPLC column (Rezex 8 u8% H, Monosaccharides), maintained at 50° C. fitted with a refractive index (RI) detector (ERC-7515A, RI Detector (Anspec Company Inc.). Saccharides were separated based on molecular weight. A designation of DP1 is a monosaccharide, such as glucose; a designation of DP2 is a disaccharide, such as maltose; a designation of DP3 is a trisaccharide, such as maltotriose and the designation "DP4$^+$" is an oligosaccharide having a degree of polymerization (DP) of 4 or greater.

Alpha amylase activity (AAU) was determined by the rate of starch hydrolysis, as reflected in the rate of decrease of iodine-staining capacity measured spectrophotometrically. One AAU of alpha-amylase activity is the amount of enzyme required to hydrolyze 10 mg of starch per min under standardized conditions.

Alpha-amylase activity was determined as soluble starch unit (SSU) and is based on the degree of hydrolysis of soluble potato starch substrate (4% DS) by an aliquot of the enzyme sample at pH 4.5, 50° C. The reducing sugar content is measured using the DNS method as described in Miller, G. L. (1959) Anal. Chem. 31:426-428. Alpha amylase activity in Liquifon Units (LU) for SPEZYME FRED was measured according to the method disclosed in U.S. Pat. No. 5,958,739. In brief, the assay method uses p-nitrophenyl maltoheptoside as a substrate with the non-reducing terminal sugar chemically blocked. The rate of p-nitrophenyl release is proportional to alpha amylase activity and release is monitored at 410 nm. Activity is calculated against a standard control.

Glucoamylase Activity Units (GAU)=The PNPG assay is used to measure the activity of glucoamylase.

Acid Fungal Protease activity (SAPU)=acid fungal protease activity is based on the release of solubilized casein peptides from a 30 minute proteolytic hydrolysis of a Purified High nitrogen Casein Substrate at pH 3.0 and 37° C. Unhydrolyzed substrate is precipitated with trichloroacetic acid and removed by filtration. Solubilized casein is then measured spectrophotometrically. One Spectrophotometer Acid Protease Unit (SAPU) is that activity which will liberate 1 micromole of tyrosine equivalent per min per gram of enzyme product under the conditions of the method.

Example 1

Effect of a TrGA, AkAA and AFP Blend or Composition on Ethanol Fermentation

This example shows the surprising usefulness of blends of glucoamylase, alpha amylase and acid fungal protease in ethanol fermentation.

The effect of acid fungal protease (FERMGEN™ from Genencor-Danisco) and an acid stable alpha amylase (AkAA having SEQ ID NO: 5) with glucoamylase (*Trichoderma reesei* or *A. niger*) was analyzed during yeast fermentation on the carbon conversion efficiency (alcohol yield). Medium containing liquefied whole ground corn was studied. Mash for this study was made-up by diluting New Energy (South Bend Ind.) liquefact (39.8% DS W/W) to 32% DS with thin stillage (9.8% DS obtained from New Energy, South Bend Ind.). The mash contained 29.3% corn DS. The mash pH was adjusted to 4.2 with 6N sulfuric acid. 600 ppm urea was added along with a Red Star Ethanol yeast inoculum. Fermentations were carried out in 500 ml flasks containing 300 gm of mash. The enzymes were diluted so that 0.2 ml was added to the flasks. All enzyme dosages were per gm of corn DS. The flasks were placed in 32° C. water bath, and occasionally mixed. The enzyme concentrations shown in Table 6 were used.

During the fermentation, approximately 2 ml samples of beer (broth) were removed for HPLC analysis. In a screw cap tube 0.5 ml of sample supernatant was added to 4.45 ml water and 0.05 ml of 1 N sulfuric acid. The tube was capped and placed in 75° C. water for 15 minutes to inactivate the enzyme activity. After heating, the diluted sample was filtered through a 0.2-micron filter for HPLC analysis. HPLC separation was conducted on a Phenominex acid column at 60° C. at 0.6 ml per minute mobile phase of 0.01 N sulfuric acid, using a 20-ul sample injection. After 71 hours the fermentations were terminated and the beer discarded.

The HPLC results in Table 6 show the effect of acid stable alpha amylase (AkAA) and acid fungal protease (FERMGEN/AFP) during yeast fermentation (0.25 GAU of Tr-GA/ gds corn, 32% ds, pH 4.3, 32° C.). The degree of polymerization, or DP, is the number of repeat units in an average polymer chain at time t in a polymerization reaction. The length is in monomer units. The degree of polymerization is a measure of molecular weight. Examples of DP-1 are monosaccharides, such as glucose and fructose. Examples of DP-2 are disaccharides, such as maltose and sucrose. DP-3 refers to maltotriose. DP>3 denotes polymers with a degree of polymerization of greater than 3. DP-1, DP-2, and DP-3 in Table 6 are sugars resulted from the hydrolysis of starch.

Lactic acid is an organic acid produced in the fermentation of carbohydrates by *Lactobacillus* bacteria. The production of lactic acid is a principal reason for loss of yield in contaminated ethanol fermentation. As such, lactic acid is routinely monitored. Glycerol is a byproduct of ethanol fermentations; it is routinely monitored as an indicator of yeast health.

The results of Table 6 show that when the level of AkAA in the enzyme blend increased, the rate of higher sugar reduction (>DP3) and consequently the rate of ethanol production and ultimately ethanol yield increased.

TABLE 6

| | | | | | | HPLC results | | | | | | |
|---|---|---|---|---|---|---|---|---|---|---|---|---|
| Ferm | TrGA GAU/g | AkAA SSU/g | Ferm Gen SAPU/g | Urea ppm | Hr | % W/V % DP > 3 | % W/V DP3 | % W/V DP-2 | % W/V DP-1 | % W/V Lactic | % W/V Glycerol | % V/V Ethanol |
| Mash | | | | | 0 | 21.79 | 4.51 | 3.12 | 1.24 | 0.46 | 0.59 | 0.05 |
| 1 | 0.25 | 0.00 | 0.000 | 600 | 7 | 14.49 | 4.62 | 4.71 | 3.16 | 0.48 | 0.91 | 1.65 |
| 1 | | | | | 20 | 7.21 | 0.59 | 6.80 | 0.31 | 0.49 | 1.30 | 8.69 |
| 1 | | | | | 30 | 5.33 | 0.58 | 2.52 | 0.56 | 0.49 | 1.48 | 12.19 |
| 1 | | | | | 48 | 1.97 | 0.37 | 0.39 | 0.42 | 0.49 | 1.63 | 15.97 |
| 1 | | | | | 71 | 0.94 | 0.23 | 0.32 | 0.05 | 0.46 | 1.62 | 16.83 |
| 2 | 0.25 | 0.50 | 0.000 | 600 | 7 | 14.04 | 4.82 | 5.14 | 3.29 | 0.47 | 0.88 | 1.59 |
| 2 | | | | | 20 | 6.96 | 0.65 | 7.22 | 0.31 | 0.48 | 1.29 | 8.50 |
| 2 | | | | | 30 | 4.84 | 0.62 | 3.11 | 0.78 | 0.49 | 1.47 | 11.97 |
| 2 | | | | | 48 | 1.73 | 0.42 | 0.42 | 0.63 | 0.50 | 1.63 | 15.69 |
| 2 | | | | | 71 | 0.87 | 0.24 | 0.34 | 0.04 | 0.49 | 1.66 | 16.89 |
| 3 | 0.25 | 1.00 | 0.000 | 600 | 7 | 13.76 | 4.99 | 5.44 | 3.24 | 0.43 | 0.85 | 1.61 |
| 3 | | | | | 20 | 6.86 | 0.69 | 7.57 | 0.32 | 0.49 | 1.30 | 8.42 |
| 3 | | | | | 30 | 4.66 | 0.66 | 3.49 | 0.62 | 0.49 | 1.47 | 11.97 |
| 3 | | | | | 48 | 1.71 | 0.45 | 0.45 | 0.82 | 0.51 | 1.66 | 15.77 |
| 3 | | | | | 71 | 0.89 | 0.25 | 0.36 | 0.04 | 0.49 | 1.69 | 17.16 |

TABLE 6-continued

HPLC results

| Ferm | TrGA GAU/g | AkAA SSU/g | Ferm Gen SAPU/g | Urea ppm | Hr | % W/V % DP > 3 | % W/V DP3 | % W/V DP-2 | % W/V DP-1 | % W/V Lactic | % W/V Glycerol | % V/V Ethanol |
|---|---|---|---|---|---|---|---|---|---|---|---|---|
| 4 | 0.25 | 2.00 | 0.000 | 600 | 7 | 12.93 | 5.23 | 5.92 | 3.26 | 0.49 | 0.91 | 1.57 |
| 4 | | | | | 20 | 6.61 | 0.74 | 7.94 | 0.33 | 0.51 | 1.32 | 8.42 |
| 4 | | | | | 30 | 4.25 | 0.71 | 3.86 | 0.63 | 0.50 | 1.50 | 12.05 |
| 4 | | | | | 48 | 1.49 | 0.46 | 0.45 | 0.49 | 0.49 | 1.64 | 16.09 |
| 4 | | | | | 71 | 0.89 | 0.26 | 0.36 | 0.04 | 0.48 | 1.68 | 17.43 |
| 5 | 0.25 | 3.00 | 0.000 | 600 | 7 | 11.94 | 5.46 | 6.73 | 3.35 | 0.48 | 0.89 | 1.61 |
| 5 | | | | | 20 | 6.28 | 0.76 | 8.49 | 0.35 | 0.48 | 1.30 | 8.47 |
| 5 | | | | | 30 | 3.92 | 0.74 | 4.05 | 0.93 | 0.48 | 1.47 | 12.03 |
| 5 | | | | | 48 | 1.42 | 0.48 | 0.48 | 1.06 | 0.50 | 1.65 | 15.81 |
| 5 | | | | | 71 | 0.89 | 0.26 | 0.37 | 0.04 | 0.50 | 1.69 | 17.37 |
| 6 | 0.25 | 0.00 | 0.025 | 600 | 7 | 14.59 | 4.64 | 4.69 | 3.23 | 0.46 | 0.86 | 1.59 |
| 6 | | | | | 20 | 7.37 | 0.62 | 6.85 | 0.29 | 0.49 | 1.28 | 8.77 |
| 6 | | | | | 30 | 5.42 | 0.57 | 2.60 | 0.45 | 0.51 | 1.45 | 12.23 |
| 6 | | | | | 48 | 2.01 | 0.38 | 0.39 | 0.31 | 0.50 | 1.56 | 15.96 |
| 6 | | | | | 71 | 0.91 | 0.23 | 0.31 | 0.04 | 0.48 | 1.55 | 16.97 |
| 7 | 0.25 | 0.50 | 0.025 | 600 | 7 | 14.03 | 4.81 | 5.17 | 3.32 | 0.48 | 0.90 | 1.59 |
| 7 | | | | | 20 | 7.09 | 0.66 | 7.17 | 0.30 | 0.51 | 1.30 | 8.72 |
| 7 | | | | | 30 | 4.81 | 0.62 | 2.94 | 0.52 | 0.47 | 1.41 | 12.35 |
| 7 | | | | | 48 | 1.60 | 0.39 | 0.41 | 0.35 | 0.49 | 1.57 | 16.19 |
| 7 | | | | | 71 | 0.90 | 0.23 | 0.33 | 0.04 | 0.47 | 1.57 | 17.22 |
| 8 | 0.25 | 1.00 | 0.025 | 600 | 7 | 13.47 | 4.89 | 5.35 | 3.25 | 0.46 | 0.85 | 1.55 |
| 8 | | | | | 20 | 6.86 | 0.69 | 7.34 | 0.31 | 0.49 | 1.27 | 8.68 |
| 8 | | | | | 30 | 4.55 | 0.65 | 3.21 | 0.56 | 0.49 | 1.41 | 12.24 |
| 8 | | | | | 48 | 1.54 | 0.41 | 0.42 | 0.66 | 0.50 | 1.58 | 16.13 |
| 8 | | | | | 71 | 0.89 | 0.25 | 0.34 | 0.04 | 0.49 | 1.59 | 17.09 |
| 9 | 0.25 | 2.00 | 0.025 | 600 | 7 | 12.46 | 5.08 | 5.79 | 3.23 | 0.45 | 0.84 | 1.56 |
| 9 | | | | | 20 | 6.70 | 0.75 | 7.87 | 0.32 | 0.51 | 1.32 | 8.93 |
| 9 | | | | | 30 | 4.01 | 0.68 | 3.43 | 0.59 | 0.48 | 1.40 | 12.02 |
| 9 | | | | | 48 | 1.37 | 0.41 | 0.43 | 0.58 | 0.48 | 1.55 | 16.09 |
| 9 | | | | | 71 | 0.89 | 0.25 | 0.35 | 0.08 | 0.49 | 1.61 | 17.18 |
| 10 | 0.25 | 3.00 | 0.025 | 600 | 7 | 11.95 | 5.39 | 6.27 | 3.22 | 0.47 | 0.88 | 1.58 |
| 10 | | | | | 20 | 6.29 | 0.76 | 7.85 | 0.32 | 0.50 | 1.28 | 8.60 |
| 10 | | | | | 30 | 3.91 | 0.74 | 3.77 | 0.79 | 0.49 | 1.43 | 12.37 |
| 10 | | | | | 48 | 1.33 | 0.43 | 0.43 | 0.25 | 0.50 | 1.59 | 16.53 |
| 10 | | | | | 71 | 0.88 | 0.26 | 0.34 | 0.08 | 0.47 | 1.58 | 17.22 |
| 11 | 0.25 | 0.00 | 0.050 | 600 | 7 | 14.60 | 4.71 | 4.84 | 3.33 | 0.48 | 0.91 | 1.66 |
| 11 | | | | | 20 | 7.33 | 0.63 | 6.73 | 0.30 | 0.50 | 1.27 | 8.95 |
| 11 | | | | | 30 | 5.27 | 0.57 | 2.39 | 0.43 | 0.50 | 1.42 | 12.59 |
| 11 | | | | | 48 | 1.93 | 0.35 | 0.39 | 0.24 | 0.50 | 1.55 | 16.26 |
| 11 | | | | | 71 | 0.95 | 0.23 | 0.31 | 0.07 | 0.46 | 1.51 | 16.88 |
| 12 | 0.25 | 0.50 | 0.050 | 600 | 7 | 13.93 | 4.81 | 5.19 | 3.33 | 0.47 | 0.88 | 1.63 |
| 12 | | | | | 20 | 6.95 | 0.66 | 7.01 | 0.30 | 0.46 | 1.24 | 8.79 |
| 12 | | | | | 30 | 4.77 | 0.63 | 2.84 | 0.51 | 0.49 | 1.41 | 12.51 |
| 12 | | | | | 48 | 1.55 | 0.37 | 0.41 | 0.39 | 0.49 | 1.54 | 16.33 |
| 12 | | | | | 71 | 0.90 | 0.24 | 0.33 | 0.08 | 0.49 | 1.56 | 17.41 |
| 13 | 0.25 | 1.00 | 0.050 | 600 | 7 | 13.37 | 4.93 | 5.57 | 3.41 | 0.47 | 0.89 | 1.66 |
| 13 | | | | | 20 | 6.64 | 0.67 | 7.07 | 0.32 | 0.51 | 1.30 | 8.88 |
| 13 | | | | | 30 | 4.31 | 0.66 | 2.87 | 0.60 | 0.50 | 1.45 | 12.65 |
| 13 | | | | | 48 | 1.33 | 0.35 | 0.40 | 0.36 | 0.47 | 1.51 | 16.04 |
| 13 | | | | | 71 | 0.88 | 0.24 | 0.33 | 0.09 | 0.48 | 1.56 | 17.19 |
| 14 | 0.25 | 2.00 | 0.050 | 600 | 7 | 12.62 | 5.18 | 5.99 | 3.35 | 0.48 | 0.90 | 1.64 |
| 14 | | | | | 20 | 6.50 | 0.72 | 7.60 | 0.32 | 0.50 | 1.30 | 8.86 |
| 14 | | | | | 30 | 4.06 | 0.71 | 3.42 | 0.63 | 0.51 | 1.45 | 12.49 |
| 14 | | | | | 48 | 1.36 | 0.41 | 0.43 | 0.56 | 0.49 | 1.55 | 16.33 |
| 14 | | | | | 71 | 0.93 | 0.26 | 0.36 | 0.10 | 0.52 | 1.66 | 18.14 |
| 15 | 0.25 | 3.00 | 0.050 | 600 | 7 | 12.11 | 5.52 | 6.87 | 3.35 | 0.47 | 0.89 | 1.69 |
| 15 | | | | | 20 | 6.18 | 0.76 | 7.72 | 0.31 | 0.49 | 1.28 | 8.85 |
| 15 | | | | | 30 | 3.73 | 0.73 | 3.51 | 0.63 | 0.49 | 1.42 | 12.49 |
| 15 | | | | | 48 | 1.24 | 0.40 | 0.42 | 0.49 | 0.51 | 1.58 | 16.00 |
| 15 | | | | | 71 | 0.88 | 0.26 | 0.34 | 0.09 | 0.48 | 1.57 | 17.06 |
| 16 | 0.25 | 0.00 | 0.100 | 600 | 7 | 14.46 | 4.65 | 4.79 | 3.31 | 0.46 | 0.86 | 1.64 |
| 16 | | | | | 20 | 7.32 | 0.62 | 6.58 | 0.27 | 0.45 | 1.22 | 8.90 |
| 16 | | | | | 30 | 5.16 | 0.57 | 2.25 | 0.40 | 0.49 | 1.38 | 12.49 |
| 16 | | | | | 48 | 1.75 | 0.34 | 0.38 | 0.16 | 0.49 | 1.51 | 16.21 |
| 16 | | | | | 71 | 0.90 | 0.23 | 0.31 | 0.08 | 0.49 | 1.54 | 17.19 |

TABLE 6-continued

HPLC results

| Ferm | TrGA GAU/g | AkAA SSU/g | Ferm Gen SAPU/g | Urea ppm | Hr | % W/V % DP > 3 | % W/V DP3 | % W/V DP-2 | % W/V DP-1 | % W/V Lactic | % W/V Glycerol | % V/V Ethanol |
|---|---|---|---|---|---|---|---|---|---|---|---|---|
| 17 | 0.25 | 0.50 | 0.100 | 600 | 7 | 13.93 | 4.79 | 5.18 | 3.29 | 0.48 | 0.90 | 1.64 |
| 17 | | | | | 20 | 6.92 | 0.66 | 6.87 | 0.28 | 0.50 | 1.27 | 8.82 |
| 17 | | | | | 30 | 4.78 | 0.63 | 2.75 | 0.48 | 0.50 | 1.40 | 12.70 |
| 17 | | | | | 48 | 1.51 | 0.37 | 0.40 | 0.27 | 0.49 | 1.52 | 16.26 |
| 17 | | | | | 71 | 0.89 | 0.24 | 0.32 | 0.09 | 0.49 | 1.55 | 17.38 |
| 18 | 0.25 | 1.00 | 0.100 | 600 | 7 | 13.40 | 4.91 | 5.49 | 3.32 | 0.47 | 0.87 | 1.66 |
| 18 | | | | | 20 | 6.69 | 0.67 | 7.05 | 0.28 | 0.49 | 1.26 | 8.90 |
| 18 | | | | | 30 | 4.37 | 0.65 | 2.92 | 0.53 | 0.49 | 1.40 | 12.54 |
| 18 | | | | | 48 | 1.38 | 0.36 | 0.42 | 0.26 | 0.50 | 1.54 | 16.53 |
| 18 | | | | | 71 | 0.87 | 0.24 | 0.33 | 0.10 | 0.48 | 1.53 | 17.32 |
| 19 | 0.25 | 2.00 | 0.100 | 600 | 7 | 12.65 | 5.17 | 5.98 | 3.29 | 0.46 | 0.87 | 1.66 |
| 19 | | | | | 20 | 6.46 | 0.72 | 7.46 | 0.28 | 0.46 | 1.25 | 9.02 |
| 19 | | | | | 30 | 3.96 | 0.70 | 3.23 | 0.53 | 0.51 | 1.43 | 12.64 |
| 19 | | | | | 48 | 1.29 | 0.38 | 0.42 | 0.33 | 0.48 | 1.52 | 16.48 |
| 19 | | | | | 71 | 0.88 | 0.25 | 0.34 | 0.10 | 0.48 | 1.56 | 17.46 |
| 20 | 0.25 | 3.00 | 0.100 | 600 | 7 | 12.11 | 5.48 | 6.73 | 3.25 | 0.48 | 0.89 | 1.63 |
| 20 | | | | | 20 | 6.15 | 0.75 | 7.60 | 0.30 | 0.48 | 1.24 | 8.83 |
| 20 | | | | | 30 | 3.72 | 0.72 | 3.45 | 0.57 | 0.48 | 1.38 | 12.62 |
| 20 | | | | | 48 | 1.27 | 0.39 | 0.42 | 0.40 | 0.47 | 1.53 | 16.66 |
| 20 | | | | | 71 | 0.90 | 0.26 | 0.34 | 0.10 | 0.47 | 1.56 | 17.58 |
| 21 | 0.25 | 0.00 | 0.200 | 600 | 7 | 14.76 | 4.70 | 4.79 | 3.28 | 0.48 | 0.89 | 1.63 |
| 21 | | | | | 20 | 7.40 | 0.65 | 6.59 | 0.28 | 0.50 | 1.26 | 9.04 |
| 21 | | | | | 30 | 5.28 | 0.57 | 2.22 | 0.34 | 0.50 | 1.40 | 12.92 |
| 21 | | | | | 48 | 1.79 | 0.34 | 0.37 | 0.15 | 0.48 | 1.49 | 16.29 |
| 21 | | | | | 71 | 0.93 | 0.23 | 0.30 | 0.08 | 0.47 | 1.49 | 17.39 |
| 22 | 0.25 | 0.50 | 0.200 | 600 | 7 | 14.35 | 4.88 | 5.22 | 3.26 | 0.48 | 0.91 | 1.66 |
| 22 | | | | | 20 | 6.94 | 0.67 | 6.66 | 0.27 | 0.51 | 1.27 | 8.76 |
| 22 | | | | | 30 | 4.77 | 0.61 | 2.63 | 0.42 | 0.49 | 1.37 | 12.74 |
| 22 | | | | | 48 | 1.50 | 0.36 | 0.39 | 0.21 | 0.49 | 1.51 | 16.62 |
| 22 | | | | | 71 | 0.90 | 0.24 | 0.31 | 0.08 | 0.50 | 1.54 | 17.45 |
| 23 | 0.25 | 1.00 | 0.200 | 600 | 7 | 13.73 | 4.95 | 5.47 | 3.29 | 0.48 | 0.90 | 1.62 |
| 23 | | | | | 20 | 6.77 | 0.68 | 6.86 | 0.27 | 0.48 | 1.24 | 8.96 |
| 23 | | | | | 30 | 4.40 | 0.65 | 2.76 | 0.43 | 0.49 | 1.40 | 12.92 |
| 23 | | | | | 48 | 1.40 | 0.36 | 0.41 | 0.15 | 0.49 | 1.55 | 17.05 |
| 23 | | | | | 71 | 0.91 | 0.25 | 0.32 | 0.09 | 0.48 | 1.53 | 17.45 |
| 24 | 0.25 | 2.00 | 0.200 | 600 | 7 | 12.90 | 5.20 | 5.95 | 3.27 | 0.46 | 0.87 | 1.63 |
| 24 | | | | | 20 | 6.43 | 0.72 | 7.23 | 0.28 | 0.49 | 1.25 | 8.75 |
| 24 | | | | | 30 | 4.07 | 0.70 | 3.25 | 0.47 | 0.51 | 1.40 | 12.77 |
| 24 | | | | | 48 | 1.26 | 0.37 | 0.39 | 0.33 | 0.46 | 1.42 | 15.77 |
| 24 | | | | | 71 | 0.90 | 0.26 | 0.33 | 0.11 | 0.49 | 1.54 | 17.56 |
| 25 | 0.25 | 3.00 | 0.200 | 600 | 7 | 11.98 | 5.39 | 6.68 | 3.27 | 0.46 | 0.86 | 1.62 |
| 25 | | | | | 20 | 6.30 | 0.76 | 7.65 | 0.29 | 0.49 | 1.26 | 9.01 |
| 25 | | | | | 30 | 3.74 | 0.73 | 3.39 | 0.56 | 0.50 | 1.41 | 12.79 |
| 25 | | | | | 48 | 1.25 | 0.39 | 0.42 | 0.31 | 0.49 | 1.54 | 16.89 |
| 25 | | | | | 71 | 0.91 | 0.26 | 0.34 | 0.12 | 0.55 | 1.55 | 17.62 |

Example 2

Mass Balance Studies

The effect of acid fungal protease (FERMGEN from Danisco US, Inc, Genencor Division) and an acid stable alpha amylase (SEQ ID NO:5) with glucoamylase (*Trichoderma reesei*) during the yeast fermentation on the carbon conversion efficiency (alcohol yield) medium containing liquefied whole ground corn was further studied in mass balance studies.

Liquefact (liquified whole ground corn substrate) was prepared by adding thin stillage to whole ground corn liquefact to obtain a final DS of 32%. The pH was adjusted to 4.3 with 6N sulfuric acid. To the mash 400 ppm urea was added along with a Red Star Ethanol yeast inoculum of 0.05% by weight. The mash was divided into 1200 gram quantities and dosed with enzyme at a level of 0.325 GAU/g DS as described in Table 8. Approximately 800 grams of mash was quantitatively added to each of four one liter volumetric flasks. In addition approximately 150 grams each was put into 250 ml Erlenmeyer flasks. The one liter flasks were stoppered with rubber corks fitted with a needle to allow $CO_2$ escape, placed in a 32° C. incubator and weighed periodically. The 250 ml flasks were placed in a 32° C. forced air shaker at 150 rpm and sampled periodically for HPLC analysis. At the end of fermentation of the one liter vessels, an aliquot was removed for HPLC analysis. The contents of the flask were quantitatively transferred to 2 L Erlenmeyer flasks using approximately 500 mls DI water. The flasks were then attached to a distillation set-up and allowed to distill. Approximately 800 mls of distillate was collected in a 1 L volumetric flask and diluted to volume. A sample was then taken for HPLC analysis. The remaining residue after distillation was transferred to a tared pan and dried overnight at 104° C. The dried residue (DDGS) was collected and assayed for residual starch.

The HPLC data on the effect of AkAA and AFP concentrations at 0.325 GAU of TrGA/gds corn on the alcohol yield and composition of sugar profile during fermentation is shown in Table 7.

TABLE 7

Effect of AkAA and AFP concentrations at 0.325 GAU of TrGA/gds under yeast fermentation on the final alcohol yield.

| # | Desc. | hrs | % W/V DP > 3 | % W/V DP-3 | % W/V DP-2 | % W/V DP-1 | % W/V Lactic | % W/V Glycerol | % W/V acetic | % V/V Ethanol |
|---|---|---|---|---|---|---|---|---|---|---|
| 1 | 600:7300:240 | 16 | 8.10 | 0.65 | 7.11 | 0.43 | 0.20 | 1.44 | 0.01 | 7.98 |
|   |              | 24 | 5.48 | 0.56 | 4.47 | 0.33 | 0.17 | 1.51 | 0.00 | 10.48 |
|   |              | 40 | 1.78 | 0.31 | 0.33 | 0.11 | 0.13 | 1.60 | 0.04 | 15.91 |
|   |              | 48 | 1.15 | 0.19 | 0.26 | 0.08 | 0.10 | 1.66 | 0.07 | 15.92 |
|   |              | 64 | 1.07 | 0.18 | 0.27 | 0.12 | 0.06 | 1.72 | 0.07 | 17.29 |
| 2 | 600:5000:240 | 16 | 7.44 | 0.56 | 6.01 | 0.41 | 0.16 | 1.40 | 0.00 | 8.15 |
|   |              | 24 | 5.11 | 0.50 | 3.48 | 0.33 | 0.14 | 1.51 | 0.01 | 11.17 |
|   |              | 40 | 1.34 | 0.21 | 0.29 | 0.09 | 0.08 | 1.59 | 0.07 | 15.49 |
|   |              | 48 | 1.05 | 0.17 | 0.30 | 0.08 | 0.05 | 1.58 | 0.09 | 15.70 |
|   |              | 64 | 0.99 | 0.16 | 0.31 | 0.11 | 0.03 | 1.58 | 0.09 | 16.36 |
| 3 | 600:2500:240 | 16 | 7.84 | 0.53 | 5.57 | 0.49 | 0.18 | 1.42 | 0.00 | 8.21 |
|   |              | 24 | 5.64 | 0.48 | 3.17 | 0.35 | 0.18 | 1.56 | 0.03 | 11.20 |
|   |              | 40 | 1.46 | 0.19 | 0.26 | 0.06 | 0.10 | 1.62 | 0.05 | 15.47 |
|   |              | 48 | 1.05 | 0.15 | 0.27 | 0.05 | 0.06 | 1.60 | 0.06 | 15.85 |
|   |              | 64 | 0.98 | 0.15 | 0.31 | 0.12 | 0.06 | 1.61 | 0.08 | 16.56 |
| 4 | 600:1000:240 | 16 | 8.35 | 0.49 | 5.38 | 0.42 | 0.19 | 1.40 | 0.00 | 8.04 |
|   |              | 24 | 6.33 | 0.47 | 3.04 | 0.37 | 0.21 | 1.56 | 0.03 | 10.85 |
|   |              | 40 | 1.85 | 0.21 | 0.26 | 0.07 | 0.14 | 1.61 | 0.03 | 15.06 |
|   |              | 48 | 1.14 | 0.16 | 0.25 | 0.08 | 0.12 | 1.64 | 0.05 | 15.56 |
|   |              | 64 | 0.95 | 0.15 | 0.29 | 0.11 | 0.10 | 1.63 | 0.06 | 16.41 |
| 5 | 600:0:240    | 16 | 8.66 | 0.45 | 5.00 | 0.37 | 0.18 | 1.40 | 0.00 | 8.06 |
|   |              | 24 | 6.96 | 0.42 | 2.52 | 0.30 | 0.18 | 1.53 | 0.02 | 10.73 |
|   |              | 40 | 2.37 | 0.22 | 0.25 | 0.10 | 0.13 | 1.58 | 0.05 | 14.55 |
|   |              | 48 | 1.28 | 0.16 | 0.23 | 0.06 | 0.07 | 1.54 | 0.04 | 15.21 |
|   |              | 64 | 1.03 | 0.14 | 0.27 | 0.07 | 0.05 | 1.59 | 0.08 | 16.15 |

The ratios shown in Table 8 under the column entitled "Desc." are GAU:SSU:SAPU.

The data in Table 8 showed that the addition of the acid fungal protease (AFP) resulted in an increased rate of alcohol production, but addition of alpha amylase (AkAA) produced even higher alcohol production as compared to the control. The mass balance data summarized in Table 8 showed that the triple enzyme blend containing TrGA, AFP and AkAA resulted in higher carbon conversion efficiency (2, 67%) compared to TrGA in combination with AFP or AkAA alone.

TABLE 8

Mass Balance data from yeast fermentation with different enzyme ratio

| # | Description | GA:SSU:SAPU | GPB Ethanol HPLC | GPB Ethanol CO2 | GPB Ethanol Distil. | DDGS lb/bu | Residual Starch |
|---|---|---|---|---|---|---|---|
| 1 | NBA2 | 600:7300:240 | 2.47 | 2.66 | 2.45 | 18.43 | 6.89 |
| 2 | NBA3 | 600:5000:240 | 2.43 | 2.66 | 2.45 | 18.49 | 5.28 |
| 3 | NBA4 | 600:2500:240 | 2.40 | 2.64 | 2.44 | 18.51 | 5.43 |
| 4 | NBA5 | 600:1000:240 | 2.37 | 2.64 | 2.38 | 18.52 | 6.22 |
| 5 | NBA6 | 600:0:240 | 2.37 | 2.59 | 2.37 | 19.19 | 7.60 |

Alcohol yield from distillation showed the same trend as the $CO_2$ values showing that the blends containing 7300 and 5000 SSU/g alpha amylase were equivalent to each other and better than the control in terms of end value for gallons of ethanol per bushel of corn (see Table 8). The data in Table 8 show that increasing the dose of AkAA increased the level of ethanol at the end of fermentation. The HPLC analysis of the final beer well showed the same trend, however not to the degree of the $CO_2$ and distillation values.

The final alcohol concentrations obtained using different enzyme compositions under the yeast fermentation conditions using liquefied whole ground corn was compared against TrGA and shown in FIG. 1. FIG. 1 showed the effect of acid fungal protease (SAPU) and acid stable alpha amylase (SSU) addition to TrGA on the final alcohol yield during yeast fermentation of liquefied whole ground corn. The different enzyme mixtures as numbered in the FIGURE were: 1:TrGA, 0.25 GAU/gds corn, 2: No #1+0.05 SAPU AFP/gds corn, 3: No #1+2.0 SSU Alpha amylase/gds.corn, and 4: No #1+0.05 SAPU, AFP+2.0 SSU Alpha amylase/gds corn.

The results unexpectedly showed that the carbon conversion efficiency (alcohol yield per gram of corn ds) depended upon the enzyme blend composition. The increase in the alcohol yield with TrGA containing AFP or AkAA was not additive, but showed unexpected, synergistic benefits.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition comprising a glucoamylase, an acid stable alpha amylase, and an acid fungal protease, wherein the ratio of the glucoamylase, an acid stable alpha amylase, and an acid fungal protease is 1:1.5:0.1 to 1:8:1, as measured by glucoamylase units: soluble starch units: spectrophotometric acid protease units (GAU:SSU:SAPU).

2. The composition according to claim 1, wherein the ratio of the glucoamylase, an acid stable alpha amylase, and an acid fungal protease is 1:2:0.2 to 1:5:0.6, as measured by GAU:SSU:SAPU.

3. The composition according to claim 1, wherein the glucoamylase is obtained from a fungus selected from the group consisting of a *Trichoderma*, a *Taleromyces*, a *Penicillium*, an *Aspergillus*, and a *Humicola*.

4. The composition according to claim 1, wherein the glucoamylase comprises an amino acid sequence having at least 90% identity with the amino acid sequence of SEQ ID NO: 1.

5. The composition according to claim 4, wherein the glucoamylase comprises the amino acid sequence of SEQ ID NO: 1.

6. The composition according to claim 1, wherein the acid stable alpha amylase is obtained from *Trichoderma* or *Aspergillus*.

7. The composition according to claim 1, wherein the acid stable alpha amylase comprises an amino acid sequence having at least 90% identity with the amino acid sequence of SEQ ID NO: 5, 7, 9, 10, or 13.

8. The composition according to claim 7, wherein the acid stable alpha amylase comprises the amino acid sequence of SEQ ID NO: 5.

9. The composition according to claim 1, wherein the acid fungal protease is obtained from a *Trichoderma*.

10. The composition according to claim 1, wherein the acid fungal protease comprises an amino acid sequence having at least 90% identity with the amino acid sequence of SEQ ID NO: 14.

11. The composition according to claim 10, wherein the acid fungal protease comprises the amino acid sequence of SEQ ID NO: 14.

12. The composition according to claim 1, further comprising an additional enzyme selected from the group consisting of: a second glucoamylase, a second alpha amylase, a cellulose, a hemicellulase, a xylanase, a second protease, a phytase, a pullulanase, a beta amylase, a lipase, a cutinase, a pectinase, a beta-glucanase, a galactosidase, an esterase, a cyclodextrin transglycosyltransferase, and combinations thereof.

13. A method for producing end products from fermentable sugars, comprising the steps of:
   a. contacting a slurry comprising a milled grain that contains starch with an alpha amylase to produce a liquefact;
   b. contacting the liquefact with a glucoamylase, an acid stable alpha amylase, and an acid fungal protease, to produce fermentable sugars, wherein the ratio of the glucoamylase, the acid stable alpha amylase, and the acid fungal protease is about 1:1.5:0.1 to about 1:8:1, as measured by GAU:SSU:SAPU; and
   c. fermenting the fermentable sugars in the presence of a fermenting organism to produce end products.

14. The method according to claim 13, wherein said end product is an alcohol.

15. The method according to claim 13, wherein steps (b) and (c) occur sequentially.

16. The method according to claim 13, wherein steps (b) and (c) occur simultaneously.

17. The method according to claim 13, wherein step (b) is carried out at 30-65° C. and at pH 3.0-6.5.

18. The method according to claim 13, wherein step (c) is carried out at 15-40° C. and at pH 3.0-6.5.

* * * * *

(12) EX PARTE REEXAMINATION CERTIFICATE (9704th)
United States Patent
Breneman et al.

(10) Number: US 8,048,657 C1
(45) Certificate Issued: Jun. 12, 2013

(54) ENZYME COMPOSITIONS COMPRISING A GLUCOAMYLASE, AN ACID STABLE ALPHA AMYLASE, AND AN ACID FUNGAL PROTEASE

(75) Inventors: Suzanne Breneman, Orfordville, WI (US); Oreste J. Lantern, Jr., Trimble, MO (US); Jayarama K. Shetty, Pleasanton, CA (US)

(73) Assignee: Danisco US Inc., Genencor Division, Palo Alto, CA (US)

Reexamination Request:
No. 90/012,161, Feb. 23, 2012

Reexamination Certificate for:
Patent No.: 8,048,657
Issued: Nov. 1, 2011
Appl. No.: 12/250,789
Filed: Oct. 14, 2008

Related U.S. Application Data

(60) Provisional application No. 60/981,035, filed on Oct. 18, 2007.

(51) Int. Cl.
*C12P 7/14* (2006.01)
*C12N 9/00* (2006.01)
*C12N 9/30* (2006.01)
*C12N 9/34* (2006.01)
*C12N 1/20* (2006.01)
*C12N 15/00* (2006.01)

(52) U.S. Cl.
USPC ........... 435/162; 435/205; 435/183; 435/203; 435/320.1; 435/252.3; 536/23.2

(58) Field of Classification Search
None
See application file for complete search history.

(56) References Cited

To view the complete listing of prior art documents cited during the proceeding for Reexamination Control Number 90/012,161, please refer to the USPTO's public Patent Application Information Retrieval (PAIR) system under the Display References tab.

*Primary Examiner* — Bruce Campell

(57) ABSTRACT

The present invention relates to an enzyme blend composition comprising a glucoamylase, an acid stable alpha amylase, and an acid fungal protease. The present invention is further directed to a method for producing end products such as alcohols from fermentable sugars, comprising the steps of: (a) contacting a slurry comprising a milled grain that contains starch with an alpha amylase to produce a liquefact; (b) contacting the liquefact with a glucoamylase, an acid stable alpha amylase, and an acid fungal protease, to produce fermentable sugars; and (c) fermenting the fermentable sugars in the presence of a fermenting organism to produce end products.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13-18 is confirmed.

Claims 1 and 2 are determined to be patentable as amended.

Claims 3-12, dependent on an amended claim, are determined to be patentable.

New claims 19-21 are added and determined to be patentable.

1. A composition comprising a glucoamylase, an acid stable alpha amylase, and an acid fungal protease, wherein the ratio of the glucoamylase, an acid stable alpha amylase, and an acid fungal protease is [1:1.5:0.1 to 1:8:1] *1:5:0.6 to 1:8:1*, as measured by glucoamylase units: soluble starch units: spectrophotometric acid protease units (GAU:SSU:SAPU).

2. The composition according to claim 1, wherein the ratio of the glucoamylase, an acid stable alpha amylase, and an acid fungal protease is [1:2:0.2 to 1:5:0.6] *1:5:0.7 to 1:8:1*, as measured by GAU:SSU:SAPU.

*19. The method according to claim 13, wherein the ratio of the glucoamylase, an acid stable alpha amylase, and an acid fungal protease is about 1:5:0.6 to about 1:8:1, as measured by GAU:SSU:SAPU.*

*20. The method according to claim 13, wherein the ratio of the glucoamylase, an acid stable alpha amylase, and an acid fungal protease is about 1:5:0.7 to about 1:8:1, as measured by GAU:SSU:SAPU.*

*21. The method of claim 13, wherein the liquefact is contacted with urea in step (b).*

\* \* \* \* \*